United States Patent [19]
Taylor et al.

[11] Patent Number: 5,925,054
[45] Date of Patent: Jul. 20, 1999

[54] PERFUSION DEVICE FOR MAINTAINING BLOOD FLOW IN A VESSEL WHILE ISOLATING AN ANASTOMOSIS

[75] Inventors: Charles S. Taylor, San Francisco; Alfredo R. Cantu, Fremont; Son M. Gia; Jeff A. Krolic, both of San Jose, all of Calif.; Robert G. Matheny, Carmel, Ind.; Amr Salahieh, Campbell; Ivan Sepetka, Los Altos, both of Calif.

[73] Assignee: Cardiothoracic Systems, Inc., Cupertino, Calif.

[21] Appl. No.: 08/790,827

[22] Filed: Jan. 23, 1997

Related U.S. Application Data

[63] Continuation-in-part of application No. 08/603,415, Feb. 20, 1996.

[51] Int. Cl.⁶ .................................................. A61B 17/08
[52] U.S. Cl. .......................... 606/153; 606/108; 606/191; 623/1; 623/12
[58] Field of Search ..................................... 606/108, 153, 606/191, 192, 195, 198; 623/1, 12

[56] References Cited

U.S. PATENT DOCUMENTS

| | | |
|---|---|---|
| 4,168,708 | 9/1979 | Lepley, Jr. et al. . |
| 4,230,119 | 10/1980 | Blum . |
| 4,483,339 | 11/1984 | Gillis . |
| 5,034,001 | 7/1991 | Garrison et al. . |
| 5,036,868 | 8/1991 | Berggren et al. . |
| 5,071,407 | 12/1991 | Termin et al. . |
| 5,087,247 | 2/1992 | Horn et al. . |
| 5,242,399 | 9/1993 | Lau et al. . |
| 5,323,789 | 6/1994 | Berggren et al. . |
| 5,328,471 | 7/1994 | Slepian . |
| 5,368,566 | 11/1994 | Crocker . |
| 5,395,333 | 3/1995 | Brill . |
| 5,397,307 | 3/1995 | Goodin . |
| 5,403,280 | 4/1995 | Wang . |
| 5,449,372 | 9/1995 | Schmaltz et al. . |
| 5,484,412 | 1/1996 | Pierpont . |
| 5,695,504 | 12/1997 | Gifford, III et al. . |

FOREIGN PATENT DOCUMENTS

| | | |
|---|---|---|
| 0 327 325 | 1/1989 | European Pat. Off. . |
| WO97/10753 | 3/1997 | WIPO . |

OTHER PUBLICATIONS

"Intraluminal Bypass Device for Arterial Surgery," DS Feldman, JF Hunger and SL Hale *Journal of Investigative Surgery*, vol. 3, pp. 169–176.

"Mammary Artery–Coronary Artery Anastomosis as Method of Treatment for Angina Pectoris," V. I. Kolesov, M.D. *Thoracic and Cardiovascular Surgery*, vol. 54, No. 4, Oct., 1967, pp. 535–544.

"Use of the Doubly Tapered Graft for the Creation of a Systemic–Pulmonary Arterial Shunt," NS Braunwald and AR Castaneda *The Annals of Thoracic Surgery*, vol. 22, No. 3, Sep. 1976, pp. 239–244.

(List continued on next page.)

*Primary Examiner*—Michael Buiz
*Assistant Examiner*—Daphna Shai
*Attorney, Agent, or Firm*—Lyon & Lyon LLP

[57] ABSTRACT

A plurality of embodiments of a distal perfusion device are disclosed, which device facilitates anastomosis constructions by maintaining a dry anastomosis site while simultaneously maintaining blood flow distally in the blood vessel to prevent ischemia and reduce overall patient trauma. The perfusion device is configured for installation into a blood vessel such as a left anterior descending coronary artery through an incision therein, to which is to be grafted a distal end of a blood vessel such as an internal mammary artery. The device includes a central member of selected configuration and material, terminating at either end thereof in respective selectively tapered end members. A lumen extending through the central member and end members, and selected perforations in the end members, maintain blood flow through the perfusion device. A selected portion or portions of the device's outer circumference fit snugly within the artery in the regions beyond and/or at the anastomosis site, to maintain the latter free of blood. Several methods for deploying and removing respective embodiments of the device also are illustrated.

9 Claims, 15 Drawing Sheets

OTHER PUBLICATIONS

"Coronary Artery Grafting Without Heart Lung Bypass Using A Temporary Intracoronary Shunt," MM Levinson, G Fooks, and LR Sauvage *The Heart Surgery Forum,* Apr. 22, 1995, pp. 1–7.

"Reduced Incidence of Intraoperative Myocardial Infarction During Coronary Bypass Surgery with Use of Intracoronary Shunt Technique," AJ Franzone, E Wallsh, SH Stertzer, NP DePasquale, and MS Bruno *The American Journal of Cardiology,* vol. 39, Jun. 1977, pp. 1017–1020.

"Placement of Coronary Artery Bypass Graft Without Pump Oxygenator," WG Trapp and R Bisarya *The Annals of Thoracic Surgery,* vol. 19, No. 1, Jan. 1975.

"Technique for Using Soft, Flexible Catheter Stents in Aortocoronary Vein Bypass Operations," LG Ludington, G Kafrouni, MH Peterson, JJ VErska, A Mulder, and LA Brewer Department of Thoracic and Cardiovascular Surgery, White Memorial Center, Los Angeles, CA, pp. (Jun. 25, 1975) pp. 328–332.

"Minimally Invasive Coronary Bypass Surgery with Internal Thoracic Artery Grafting: Early Experience and Critical Analysis," SA Oliveira, JM Souza, S Rogas, LA Dallan, LA Lisboa Hospital Beneficiencia Protuguesa—Sao Paulo—Brazil, p. 44.

"Internal Vessel Occlusion: An Improved Technique for Small Vessel Anastomosis," JB Griffin, M.D. and RL Meng, M.D. *J. Vasc. Surg.,* 1986; vol. 4, pp. 616–618.

Research Medical Vascular Product Brochure entitled "Balloon, Tapered and Straight Carotid Artery Shunts. A Complete Line for Every Surgeon's Preference." (4 pgs).

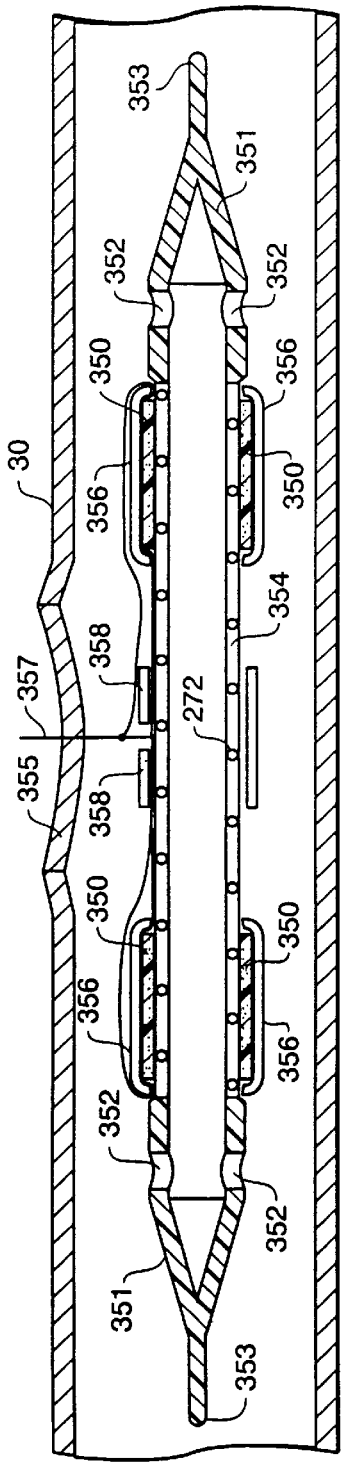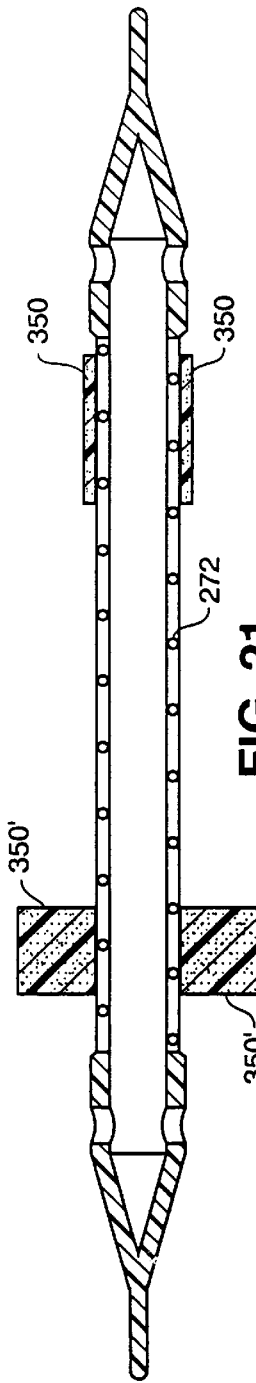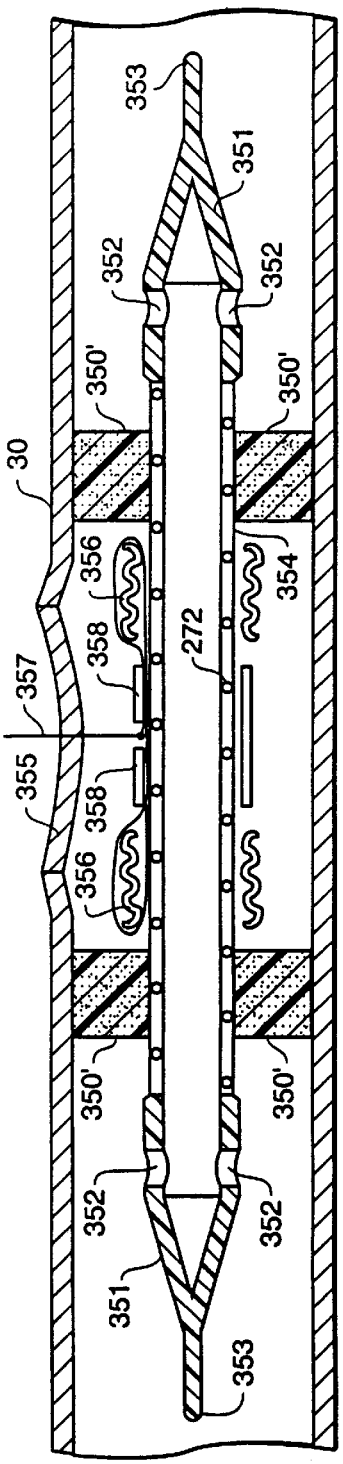

PERFUSION DEVICE FOR MAINTAINING BLOOD FLOW IN A VESSEL WHILE ISOLATING AN ANASTOMOSIS

This application is a CIP of Ser. No. 08/603,415 filed Feb. 20, 1996.

BACKGROUND OF THE INVENTION

The present invention relates principally to a perfusion device for use in performing minimally-invasive vascular microsurgeries and in particular to minimally invasive coronary artery bypass grafting (CABG) procedures such as an internal mammary artery (IMA) or vein graft to a coronary artery anastomosis procedure. The device of the invention maintains blood flow distally in a coronary artery such as the LAD during the construction of an anastomosis, thereby preventing ischemia and maintaining a dry anastomosis site to facilitate the procedure.

Surgeons are constantly striving to develop advanced surgical techniques resulting in turn in the need for developing advanced surgical devices and instruments to facilitate performance of such techniques. Recent advances in the surgical field are increasingly related to operative techniques which are less invasive and reduce overall patient trauma. To illustrate, in the field of CABG procedures it has been common practice for surgeons to perform a sternotomy where a lengthy incision is made down the middle of the chest to expose the body cavity in the thorax region, wherein retractors are employed to provide the surgeons the access required to perform the necessary bypass surgery.

However, more recent surgical techniques employ less invasive CABG procedures, known as "endoscopic" surgery, involving the use of an endoscope instrument which permits the visual inspection and magnification of any cavity in the body, such as the thorax cavity. The procedure involves the insertion of tubes called trocar cannulas through the soft tissue protecting the body cavity. The surgeon then performs diagnostic and therapeutic procedures at the surgical site with the aid of specialized micro-instrumentation designed to fit through the various trocar cannulas that provide the required openings into the body cavity.

In such endoscopic techniques, an arterial blood source such as an IMA is dissected from its location, transacted and prepared for attachment at an anastomosis site on a selected coronary artery, commonly the left anterior descending artery (LAD). To this end, a portion of the LAD is exposed and an incision is made in the arterial wall. The distal end of the IMA is then sutured over the incision in the LAD to complete the bypass graft surgery.

However, in order to perform the above surgical procedures, heart activity must be arrested. Thus, to maintain the patient, it is necessary first to divert the patient's blood circulation through an extracorporeal cardiopulmonary bypass system. This is accomplished by isolating the heart at selected arterial locations using selected catheter instruments and occluders to draw the blood into the bypass system for oxygenation thereof via an associated pump oxygenator. The oxygenated blood is returned to the patient to maintain the patient's systemic circulation during the surgery. The procedure further includes the ligating of vessels by pinching off the vessel with sutures and/or the use of occluder devices in the artery, the functions of which are to prevent the flow of blood through the artery to maintain a dry surgical site during the suturing of the anastomosis.

Accordingly, many typical cardiovascular surgical procedures, even many so-called less invasive procedures, include the procedures of placing the patient on a cardiopulmonary bypass system and then inducing cardioplegia arrest of the heart. It follows that the entire anastomosis construction is performed with the heart in the arrested state, and with special precautions taken to prevent any blood flow in the vessel on which the anastomosis surgery is being performed. To this end, an occluder device, which is sometimes inserted in the blood vessel to isolate the anastomosis site, is specifically configured to be impenetrable to the flow of fluid and to thereby prevent the flow of blood through the occluder device at the anastomosis site.

The surgical procedures of previous mention experience the disadvantages of increased trauma to the arteries caused by ligatures, to the heart due to the cessation of blood flow to distal portions thereof, and to the patient in general due to the cardiopulmonary bypass and cardioplegia arrest procedures and instruments. Accordingly, it would be highly desirable when performing a bypass surgery to circumvent the problems of previous mention, that is, to obviate the need for a cardiopulmonary bypass procedure and to allow the anastomosis construction to be performed without the occlusion of blood flow through the associated blood vessel and to prevent ischemia while still maintaining a dry anastomosis site to facilitate the suturing procedure.

An analogous problem is encountered whenever a surgical procedure penetrates the wall of a vessel. In many instances, the problem is overcome using mechanical means to occlude the vessel, either by externally clamping the vessel closed, or by use of an intravascular occluder as mentioned above. However, both approaches necessarily interrupt blood flow through the vessel, depriving the downstream tissue of oxygenated blood and creating the possibility of ischemia/reperfusion injury.

SUMMARY AND DESCRIPTION OF THE INVENTION

The present invention overcomes the above problems by enabling a surgeon to perform an anastomosis construction on, for example, a left anterior descending coronary artery (LAD) without occluding the distal flow of blood through the LAD to the heart. The invention thus facilitates the anastomosis construction by keeping the surgical site free of blood while preventing ischemia and reducing overall patient trauma.

Although the present invention is described herein in the performance of anastomosis surgery involving a graft of an internal mammary artery (IMA) to a LAD, it is to be understood that the invention and associated techniques are equally applicable to performing anastomosis constructions or surgical grafts on body vessels other than the LAD-IMA example employed herein for purposes of description.

Moreover, certain embodiments of the invention may be used in any medical application where a flow of fluid is desired to be maintained past an opening in the fluid conduit. Such applications occur in several surgical settings and other procedures both within the cardiovascular system and elsewhere.

The present invention comprises a distal perfusion device, hereinafter termed a "shunt" for ease of description, for use in LAD-IMA surgical procedures and the like. The shunt maintains blood flow in the LAD to prevent ischemia while maintaining a dry or blood free anastomosis site to facilitate a surgeon's suturing procedure. A shunt also provides support within the LAD if the LAD is ligated via sutures bordering the anastomosis site thereby decreasing trauma to the vessel. The shunt may also be configured with flanges, protruding edges, etc., to help expose the anastomosis to aid the positioning of a needle or otherwise further facilitate the suturing procedure.

To this end, the invention provides a microsurgical device, generally including a cylindrical central portion or member formed of a thin-walled, tube-like flexible material which includes a lumen therein to allow the flow of blood or other fluids through the central member. In preferred embodiments, selectively tapered end members are provided on either extremity of the central member, which extremities may be termed the proximal and distal extremities upon insertion in the LAD. The tapered end members include various configurations and perforations in the conical walls and/or in the apexes as well, as necessary to maintain the nominal blood flow through the shunt. The configuration of the opposing tapered ends facilitates the insertion of the shunt into an incision in the LAD, for example, by a surgeon using forceps. Since the shunt must be longer than the incision, that is, the anastomosis site, various shunts are installed in preferred embodiment by first inserting one end, generally of either end of the shunt, into the incision until the opposite end of the shunt clears the respective apex of the incision. The shunt is pressed into full coaxial alignment with the LAD and then is slid in the direction of the opposite end until it is centered within the LAD relative to the anastomosis site. A surgical thread or other filamentary strand may optimally be attached to the shunt at a strategic point or points to aid in the selected insertion of the shunt through the incision and into position in the LAD, as well as to aid in the selected removal of the shunt prior to conclusion of the anastomosis construction.

The central member and tapered end members may be integrally formed as by a molding process, or the end members may be individually formed and then coaxially affixed permanently to the extremities of the central member by a suitable bonding, gluing, etc., process. A number of materials are contemplated for use in accordance with the invention, wherein the material used, in part or in total, dictates the structural configuration of the shunt and the associated manner of inserting, expanding and/or contracting the particular shunt.

In preferred embodiments, the shunt may include spaced apart annular ridges located generally about the extremities of the central member to provide enlarged diameters for the shunt beyond either extremity of the anastomosis site to enhance the occlusion of blood therefrom. The ridges may be integrally formed about the central member or may comprise expandable members whose diameters are enlarged radially outward when required, generally upon insertion of the shunt in the LAD. Depending upon the material and associated structure, the expandable ridges may, or may not, subsequently be contractible to their initial diameters to facilitate the removal of the shunt.

In one configuration, the shunt is manufactured to include a means for providing structural support in at least the central member of the distal perfusion device. Preferably, the structural support means traverses the entire central member to provide increased structural support and to maintain the shape of the shunt when inserted in the vessel. In preferred embodiments of the invention, the structural support means is a coil which is embedded in a flexible material which seals the shunt along its length and the length of the central lumen disposed therein. The coil is inherently flexible and returns to its original shape after being manipulated during insertion into the vessel at the anastomosis. Although a coil is preferred, a braid, mesh, or other rigid structure such as a tube or cylinder may also be incorporated into the central member of the shunt.

The manufacture of the preferred coil embodiment may be achieved by embedding the structural support means into a thermoplastic elastomer or other fluid impermeable flexible material to obtain a conformable center section which provides structural integrity around a hollow space (lumen) traversing the center section to permit the flow of fluid, i.e., blood, therein. Preferably a thermoplastic elastomer extrusion can be drawn over a flexible coil and subsequently shrunk onto the coil, i.e., by heat treatment. The coil may also be dipped in silicone to impregnate the structural means. The coil can be formed from several materials generally considered suitable for filaments, including stainless steel, tungsten, aluminum, etc. Additionally, a synthetic coil can be formed from Kevlar and like materials.

To form a central member from a coil, particularly where the central member is sized for a typical LAD, the coil is slipped over a teflon beading mandrel with an outside diameter of approximately 0.032" and a thermoplastic elastomer (such as a polyether block amide PEBA) lumen is slipped over both the coil and mandrel. The PEBA is melted and impregnated into the coil by heating with a hot nozzle or hot dye at approximately the melt temperature for the polymer used (such as 300 at 450° F.) for about 30 seconds to one minute. The shrink tubing is manually removed to yield a reinforced central member assembly made of a coated structural means comprised of an impregnated coil.

Alternatively, the reinforced central member assembly can be made using a molding process or an extension process. The molding process can be done by applying short cycles of heat and pressure. A coextrusion process can also be used by simultaneously winding a coil into an extruder to impregnate the coil. The tips of the shunt are made in a similar fashion to the central member. A tapered mandrel is used as the inside of the mold and either a heat shrink tubing or a hot dye is used as the outside mold. Heat and pressure are necessary to flow the thermoplastic elastomer to the proper shape. The tip is drilled or punched with a sharp hypotube to create the perfusion holes. After one tip is made a mandrel is inserted through one of the perfusion holes to form the tip at the other end. Alternatively, the tips with or without holes, can be injection molded of then attached to the central member.

The device at the invention may also be expandable and may have expandable members attached to the central member by any convenient method such as by ultraviolet curing of an adhesive, a cyanoacrylate adhesive, or by solvent bonding. Where necessary, the expandable members may be compressed using a mechanical fixture or equivalent during attachment.

In preferred embodiments of this configuration, the expandable members are comprised of annular segments of expandable foam which, upon radial expansion, engage the interior walls of the vessel to prevent the flow of blood from passing out through the opening in the vessel. The foam material may be advantageously selected to expand upon contact, or shortly thereafter, with blood or other fluid so that the shunt may be manipulated with the expandable members in a substantially unexpanded state, followed by insertion into the vessel whereupon the members expand to engage the inner walls of the vessel. The expansion of the expandable members may be caused by contact with fluid such as blood by chemical treatment of the shunt, or by constructing the shunt so that insertion into a vessel causes selective exposure of the expandable members to fluid.

To provide maximum control over the timing of the expansion of the expandable members and to provide a slippery surface during insertion against the artery wall, all or a portion of the annular ridges, may be covered or surrounded by an associated structure such as a substantially fluid impermeable sheath means which is removed from about the expandable ridges upon positioning of the shunt device. The sheath means are preferably made of C-flex, a styrene ethylene butylene styrene block copolymer and are simultaneously stretched and slipped over and around the expandable members. Once the sheath means are positioned, a thread is arranged to facilitate removal of the sheath means upon placement of the shunt. In the above configurations, the shunt may be positioned such that the central member is coaxial within the vessel prior to removal of the sheath means, or expansion of the expandable members, thereby providing maximum control, minimizing the potential for trauma to the vessel, and providing a more effective seal between the shunt and the interior of the vessel at points beyond the apex of the incision. In a preferred embodiment of this configuration, the sheath means are deployed by manipulating a plurality of threads, which may be surgical sutures, and which are attached to or surround the sheath means. The thread(s) may approach the shunt substantially at the middle of the central member of the shunt (of may be offset) where one or more, and preferably two, suture guides direct the path of the thread to engage the sheath means at either end of the shunt.

In this embodiment, the central member of the shunt has associated therewith at least one (and preferably two) threaded guides which are typically offset from the center of the device and are each disposed between the center point of the lumen of the device and the expandable members at either end of the shunt device. The thread guides reduce the possibilities that the threads will become entangled with sutures used in the surgical procedure. Thread or suture guides are also used as covers and capture the sheaths after deployment in a way to minimize interference of the sheaths with sewing needles used to sew the anastomosis.

The sheath means and attached thread are preferably associated with a sheath remover which facilitates the selective removal of the sheath means from about the expandable members. The sheath remover is a small length of hollow tubing which should have a diameter less than the central member of the shunt and less than the shunt retriever described elsewhere herein. The sheath remover is traversed by the thread and facilitates the mechanical removal of the sheath means by sliding the sheath remover into abutment with the shunt. The sheaths may then be removed by drawing tension on the thread. After removal of the sheaths, the sheath remover is slid along the thread away from the arteriotomy.

In addition, a single ridge of an axial length sufficient to span the anastomosis site may be provided concentrically about the central member. The single ridge configuration preferably is an expandable member which initially is in a contracted condition to facilitate insertion. The expandable member further subsequently may be contracted to facilitate removal from the LAD.

In further embodiments, the central member itself, along with the end members which may be tapered accordingly, is selectively expandable radially outward, whereby essentially a portion of the shunt is expanded in diameter upon demand when the shunt is in place, to occlude blood from the thusly isolated anastomosis site. As in the case of the single and dual ridge embodiments of previous discussion, the material used in forming the shunt may dictate the structure of the shunt as well as its associated manner of contraction and/or expansion. Where a separate expandable member is provided in close proximity to the end members, the end members may be tapered from the most distal point backwards such that the abutment with the expandable members is substantially flush, i.e., have substantially equal outer diameters.

To illustrate, in the dual or single ridge shunt configuration, the expandable members which are formed, for example, of a hydrophilic polymer material which expands upon being converted to a hydrogel material in the presence of aqueous fluids such as hydrophilic polyurethane. The hydrogel will undergo hydration-dehydration cycles, however since the shunt is in a wet environment the material and thus the expanded ridges may not be contractible subsequently. In an alternative embodiment the ridges may be formed of annular balloons which are both expandable and contractible on demand. The single ridge configuration is provided with a partial cylindrical sheath in the region of the anastomosis to prevent puncture of the balloon by a suture needle.

In further embodiments, the central member and the tapered end members themselves are formed of the hydrophilic material which converts to a hydrogel material or hydrophilic polyurethane when wet. Alternatively, the central member is formed of an elongated annular balloon which when expanded still provides the lumen therethrough. In another embodiment, the central member is formed of a cylindrical unfolding spiral of a polymer material such as polyurethane, polyester, polyethylene, PEBA, silicone, latex, a shape memory thermoplastic, or hydrophilic polyurethane which loses a sticky property and expands to a desired diameter of, for example, from 1 to 6 millimeters (mm), upon being exposed to an aqueous fluid. Such a material and the shunt generally is not contractible after expansion.

In a further alternative embodiment, the cylindrical unfolding spiral is formed of two bonded sheets of, for example, a nickel-titanium alloy material having an inherent shape-memory property. One sheet is annealed in the shape of a tightly curled cylinder, while the other sheet is annealed as a flat or less curled sheet. A heating coil is bonded to each sheet. The shunt is formed of the bonded sheets rolled into a spiral cylinder of selected diameter. The application of a small electrical current to one coil causes the shunt to contract, while the application of a small electrical current to the other coil causes the cylindrical spiral to unfold and expand to the desired diameter.

In still a further alternative embodiment, the shunt is formed of a cylindrical braided material of selected nominal diameter. The braided material decreases in diameter relative to the nominal diameter when stretched axially, and increases in diameter relative to the nominal when compressed axially. The shunt is formed of the braided material to define a central member with tapered end members integrally formed therewith. A selected length of the central member is impregnated with an elastomer material such as silicon, latex, etc., which is impervious to fluids while still allowing axial and radial flexibility. A thread or other filamentary strand, is attached internally to either tapered end of the shunt, whereby applying a pulling force to the thread causes the braid to contract and expand, while relaxing the pulling force allows the braided material to relax and contract.

In other alternative embodiments, various configurations of flexible springs and/or coils are employed as the basic expandable and contractible structures. The coils generally are provided with a loose or compliant cover, for example, a fluid-impermeable, flexible elastomer material to provide the fluid impervious central member required to isolate the anastomosis site. In some embodiments the shunt diameter is controlled by the application of a force to a thread, thin wire, etc., which force in turn alters a natural state of the coil to produce an expansion and/or contraction.

In a modification of the various shunt embodiments, a portion is removed from the central member to define a necked-down mid section. This embodiment lends itself to an insertion procedure wherein the shunt is folded at the necked-down mid section via forceps or other insertion instruments and both tapered ends are inserted through an arteriotomy whereupon the shunt is gently unfolded into place in the artery.

In a further alternative embodiment, a shunt access member in the general shape of a tube, is formed in the central member of the shunt to extend generally radially therefrom. The tube includes a lumen therethrough which is in communication with the lumen of the shunt. Such an access member may provide support for the distal end of an IMA to facilitate the anastomosis construction and/or to maintain blood flow from the IMA to the artery or other vein or artery from the body or outside the body. Further, the access member provides access to the artery by an introducer implemented in another insertion procedure particularly applicable to such a shunt configuration.

The device of certain embodiments of the invention is of a size to fit conformingly within an arterial vessel, especially a coronary artery, and is of an overall length and diameter usually in accord with a vessel occluder rather than a mere tube-type shunt of traditional design which only permits the flow of blood therethrough. Despite the smaller dimensions of the distal-perfusion type shunt of the invention, the shunt has sufficient tensile strength to be manipulated by a surgeon using surgical tools, is flexible enough to be placed within a moving vessel without damaging the vessel or the surrounding tissues, and is structurally durable enough to maintain a shape permitting the flow of blood therethrough.

As is apparent from the description herein, the insertion and removal of the device of the invention is achieved in a manner to lessen the possibility of damaging the vessel into which the device is inserted. The shunt may readily be inserted and removed using forceps. For insertion, first, one end member of the device is inserted into the vessel by guiding the tip of one end member through the arteriotomy and then advancing one end of the device into the vessel until the holes in the first end member are within the vessel at a point beyond the incision. Similarly, the expandable members or annular ridges are advanced to a point beyond the apex edge at either end of the incision to effectively seal the device against the inside of the vessel. At this point, the central member is manipulated until the tip of the other end member can also be introduced through the arteriotomy. Once both tips and end members are inserted, the central member of the shunt is positioned within the arteriotomy to prevent the flow of blood out through the arteriotomy while permitting distal perfusion by the flow of blood through the shunt; preferably, the end members of the shunt are roughly equidistant from the center of the arteriotomy.

The device may have fixtures or separate apparatus operably associated therewith to aid in deploying and removing the shunt in a surgical setting. As noted above, a thread attached to the device, preferably in the center thereof, aids in removal. Additionally, however, one may use the thread in cooperation with additional associated fixtures to provide a shunt remover for removal and retrieval of the shunt from the vessel.

BRIEF DESCRIPTION OF THE DRAWINGS

FIG. 20 is an embodiment of the invention having two expandable members at either end of the device, surrounded by sheath means positioned with a vessel.

FIG. 21 is an embodiment of the invention having expandable members at both ends of the central member and one expandable member shown in an expanded state.

FIG. 22 shows an embodiment wherein the sheath means are deployed by manipulation of the thread to permit fluid exposure and complete expansion of the expandable members.

DETAILED DESCRIPTION OF THE PREFERRED EMBODIMENTS

As may be seen from the following description and accompanying drawings, the present invention contemplates several basic shunt configurations, with a plurality of modifications to the configurations, wherein the modifications for the most part are interchangeably useable in the various basic shunt configurations. Likewise, while several materials are particularly for use with certain shunt configurations as disclosed, the materials discussed herein may generally be used with any of the shunt configurations without departing from the spirit of the invention.

Figure 1:
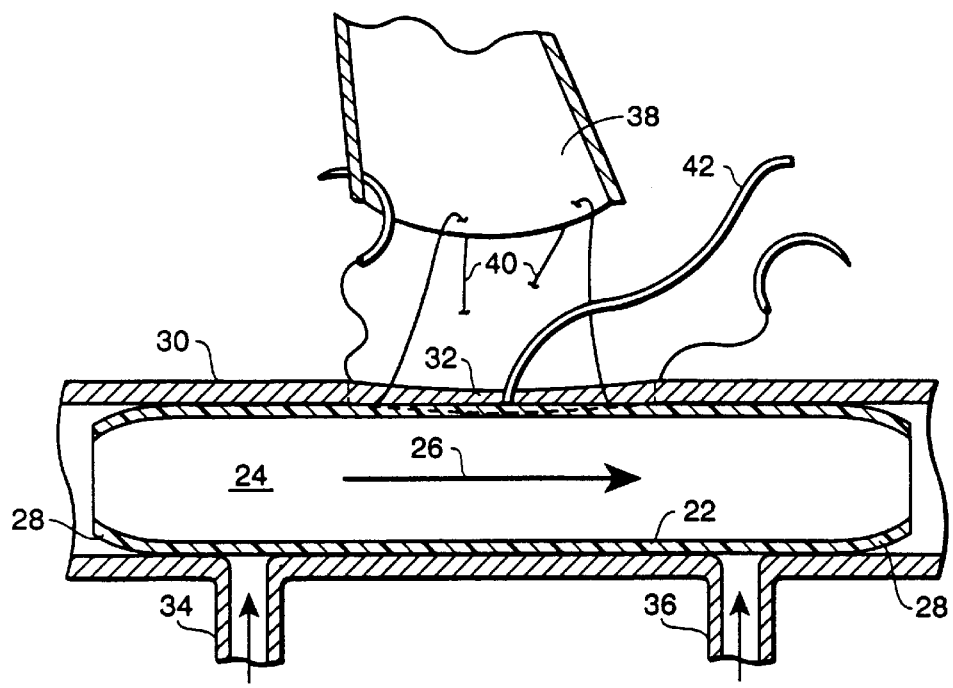
FIGS. 1 and 2 are elevational views, in cross-section, of a small segment of an artery depicting a shunt installed within the artery in accordance with the invention to isolate an anastomosis site while maintaining blood flow distally.

FIG. 1 illustrates a basic shunt 20 formed of a central member 22 having a lumen 24 therethrough for passage of blood through the shunt 20 as depicted by arrow 26. The central member 22 terminates in extremities 28 and is formed of a material such as polyurethane, polyethylene, silicon, etc. The shunt 20 is shown in FIG. 1 installed in place within, for example, an LAD artery 30 of previous mention, and particularly spanning an arteriotomy or incision 32 in the LAD which forms a site for an anastomosis construction. The shunt 20 is of sufficient outside diameter of, for example approximately 1–5 to 6 mm or any value therebetween, such that, when installed, fits snugly within the interior walls of the LAD 30 to thereby maintain the anastomosis site, corresponding to the incision 32, free from blood while allowing blood flow 26 through the LAD. As depicted, the shunt 20 not only occludes the blood from the LAD, but also occludes blood flow from possible arterial side-branches such as depicted at 34, 36.

As is well known, the anastomosis surgery consists of grafting a distal end of, for example, the internal mammary artery (IMA) 38, to the LAD 30 to encompass the incision 32. The anastomosis is performed by the surgeon by sequentially passing sutures 40 through the edges of the incision 32 and through the distal end of the IMA 38 until suture loops are made around the confronting circumference, in conventional fashion. Prior to tightening the suture loops about the circumference of the arteriotomy to secure the graft, the shunt 20 is carefully removed from within the LAD either directly or by pulling on a thread or like filamentary strand 42 or suture secured to a selected point or points on the shunt, while guiding the shunt via forceps or tweezers through the incision and adjacent loops of the sutures 40. The suture loops about the circumference of the arteriotomy are then drawn tight to provide a fluidly sealed anastomosis.

By way of example, an arteriotomy may be of the order of 6 to 12 millimeters (mm) and the perfusion devices generally are of the order of 15 to 30 mm and most often 20–25 in length, with an inside diameter generally of 0.5 to 2 mm, and most often 0.65 to 1.0 mm. and the outside diameter generally of from 1.0 to 6.0 mm. and most often 1.5 to 3.5 mm.

Figure 2:
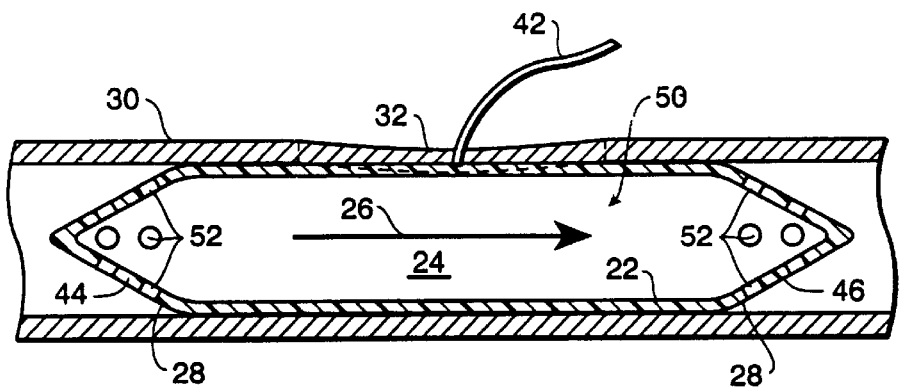

FIG. 2 depicts a modification to the shunt 20 of FIG. 1, namely the addition of more pronounced tapered end members 44, 46 to the extremities 28 of the central member 22, to form a generally symmetrically tapered shunt 50. The end members are formed of the same material as the central member 22, or may be formed separately of a material of different stiffness and then bonded, glued, etc., to the central member 22. The taper angle of the end members 44, 46 may vary from a slight taper with a relatively large apex opening such as in FIG. 1, to a sharp taper extending to a closed apex to form a tip distal to the openings or perforations 52 as in FIG. 2 or to the open apex of FIG. 1. The tapered end members 44, 46 are provided with a selected array of openings on perforations 52, the number and arrangement of which are variable to provide the nominal blood flow desired for the particular surgical application.

Figure 3:
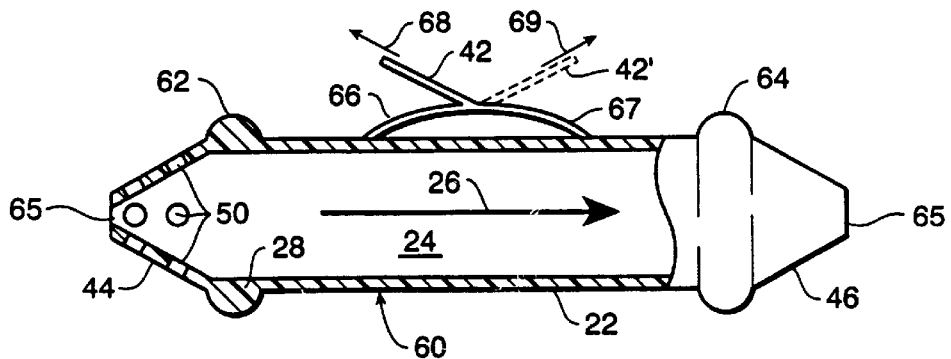
FIGS. 3, 4 and 6 are elevational views, in cross-section, of alternative embodiments of the present invention depicting additional configurations and modifications of the invention of FIGS. 1, 2.

FIG. 3 depicts an alternative embodiment of the invention wherein the shunt 50 of FIG. 2 is modified to provide a shunt 60 having annular ridges 62, 64 formed about generally the extremities 28 of the central member 22. The ridges may be integral and formed of the same material as is the central and tapered end members 22, 44, 46 and as such are formed with pre-selected diameters. Alternatively, the ridges may be expandable members which are formed of other materials and/or of devices which are expandable as well as contractible as further described below in alternative embodiments. To illustrate, the annular ridges 62, 64 may be formed of the hydrophilic polymer material such as a soft shape memory thermoplastic that may be activated at body temperature or a hydrophilic polyurethane which, due to its disposition about the extremities 28 of the central member 22, expands radially outward as it converts to a hydrogel material upon being inserted in the aqueous fluid environment of the LAD.

Exposure of the expanding materials to fluid my be achieved by several alternative means including providing a removable covering for the material and generally disposed about the annular ridges 62, 64 (in an embodiment of FIG. 2) as described in greater detail below. Alternatively, the central member 22 in end members 44, 46 may have an integral opening or channel (not shown) formed therein such that fluid such as blood contacts the expanding materials upon insertion into the vessel, such as the LAD artery 30. Moreover, the expandable materials may be provided with a covering, such as the sheath means described in greater detail below, which is permanently affixed about the end members and which is permeable or semi-permeable to fluid. This embodiment provides an expandable end member 44, 46 for the device whereby the expansion occurs automatically upon insertion of the device into the anastomosis site (incision) 32. Other triggerable expanding polymer materials may be used as well such as open cell foam, etc. The enlarged ridges provided by the expandable materials provide enhanced contact with the interior wall of the LAD to maximize the isolation of the anastomosis site. Note that the apexes formed at the tips of the tapered end members 44, 46 herein are depicted open at 65 to allow added blood flow, if desired, in addition to the openings or perforations 52. In FIG. 3, the filamentary strand 42 is attached at two spaced apart points of the central member 22 via diverging strands 66, 67. Such a dual-point strand configuration aids in the shunt insertion process, particularly when the surgeon initially inserts, for example, the end member 44 into the incision (32, FIGS. 1, 2) by pulling gently on the combined strands 42, 67 as depicted by arrow 68 toward the proximal end of the shunt 60 while urging the shunt with forceps. Once the distal end member 46 clears the incision, the shunt 60 is urged distally in the LAD with forceps and by pulling gently on the combined strands 42, 66 as depicted by arrow 69. Such a dual-point filamentary strand connection may be employed in other shunt embodiments described herein if desired or a single strand configuration may be used as described in greater detail herein.

Figure 4:
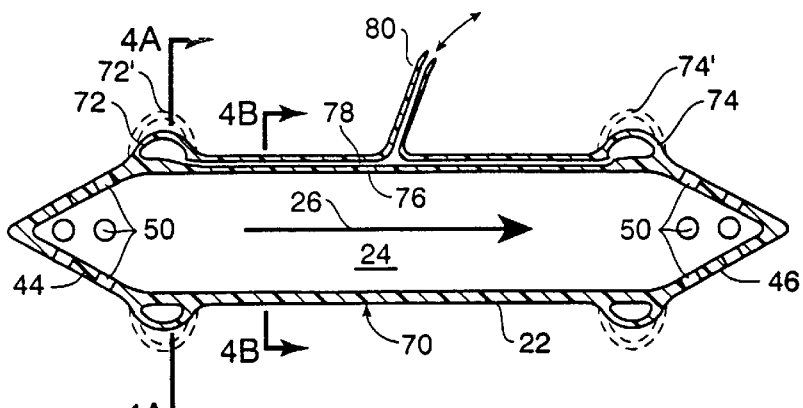

FIG. 4 depicts a shunt 70 similar in configuration to the shunt 60 of FIG. 3 but including the modification comprising selectively expandable dual ridges defined by expandable "balloons" 72, 74 which herein are integrally formed with the central and tapered end members 22, 44, 46 as shown. However, the expandable dual ridges may be provided as a separately formed assembly coaxially assembled about generally the central member, as further described in FIG. 5. As shown further in FIGS. 4A, 4B, the central member 22 includes an axially extending thickened upper section 76 within which is formed a lumen 78 which extends the length of the central member to open into respective chambers of the expandable balloons 72, 74. The lumen 78 is depicted in communication with a centrally located fluid supply tube 80 through which air, saline fluid, etc., may be supplied on demand to the balloons 72, 74 to expand them radially outward to desired diameters 72, 74, shown in phantom line. As may be seen, the dual balloons may be contracted to a reduced diameter on demand by removing the supply of fluid, or by applying a selected source of vacuum. If a centrally located supply tube such as tube 80 is used to supply the fluid on demand to the expandable balloons 72, 74, it is preferable to form the balloons of a non-compliant material, that is, a material which expands to a limit and expands no further even with the introduction of additional pressure. The use of a compliant material, such as silicon or latex, with a single supply tube could result in the expansion of one balloon but not of the other. However, a compliant material may be used if the central lumen 78 is omitted and two supply tubes supply the expansion fluid directly to respective expandable balloons 72, 74.

Figure 4A:
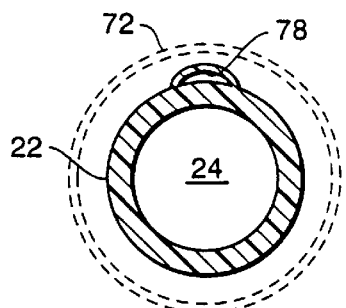
FIGS. 4A and 4B are cross-sectional views taken along section lines 4A and 4B respectively, of FIG. 4.
Figure 4B:
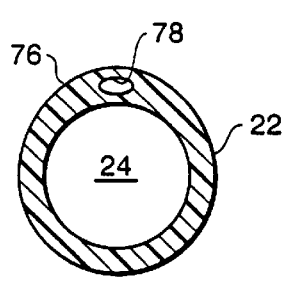

The supply tube 80 may be advantageously used with the device of this invention for several purposes in addition to supplying air, fluid for the selective inflation of balloon members. The supply tube 80 may have open ports (not shown) which allow fluid to flow around the device and the incision 32 of the anastomosis site such as for irrigation, to expose the edges of the arteriotomy, etc. Thus, the supply 80 tube or tubes may perform several functions, and including shunt removals, may, as seen in FIGS. 4A and 4B, be in communication with a lumen 78 which may be integral with the body of the central member 22. Where the lumen 78 terminates in an open part (not shown) or parts, the location of the open parts is dictated by the desired function. Where the parts facilitate irrigation, the parts will preferably be proximal to the central member 22 of the device, near the edges of the arteriotomy, and open to the external portion of the central member 22 proximal to any structure, such as balloon 72, 74 or annular ridges 62, 64, which seal about the interior of the vessel. Likewise, for drug delivery, the opening may be external of the central member 22 or internal to deliver drugs directly into the distal perfusion provided by the device during the surgical procedure.

Figure 5:
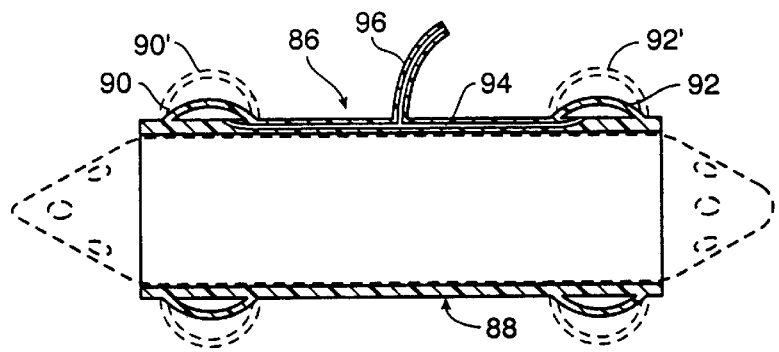
FIG. 5 is an elevational view, in cross-section, of a dual balloon configuration such as employed in the shunt embodiment of FIG. 4, illustrating one construction thereof and the manner of assembly about a shunt central member.

FIG. 5 depicts an alternative construction for providing the expandable dual balloon configuration illustrated in FIG. 4. The configuration of FIG. 5 is a separate dual balloon assembly 86 in the form of a tube-like structure which can be coaxially slid over a pre-formed shunt, such as shunts 20 and 50 of FIGS. 1 and 2, and bonded, glued, etc., to the exterior cylindrical wall of the shunt (shown herein in phantom line). The assembly 86 is formed of a central member 88 of a selected material such as polyethylene, polyurethane, polyester, etc. Expandable balloons 90, 92 formed of the same or a different material are bonded, glued, molded, etc., to respective ends of the central member 88 to define a unitary tube-like structure. An upper axial portion of the cross-section of the central member is thickened to allow the formation therethrough of a lumen 94 which communicates with respective chambers of the balloons 90, 92. A fluid supply tube 96 is formed in communication with the lumen 94 to supply or extract the air or other expansion fluid to the balloons 90, 92 on demand. In their expanded condition, the balloons 90, 92 expand radially outward to a desired diameter 90, 92, depicted in phantom line. In the example of FIG. 5, the sealed chambers of the balloons 90, 92 are formed after the assembly 86 is sealed to a shunt, however the balloons may be formed with respective internal cylindrical walls to define a totally sealed chambers/balloons assembly 86 prior to assembly about a shunt.

As may be seen, the configuration of the balloons 90, 92, lumen 94 and supply tube 96 resemble the configuration of the equivalent elements of FIGS. 4, 4A, 4B. As discussed previously relative to FIG. 4, the material used to form the balloons 90, 92 may be non-compliant or compliant with one or two supply tubes 96, respectively, coupled thereto, and, optimally, providing the various functions as described above.

Indicator and valve mechanisms may be employed to effect a controlled expansion of the outer diameters of the balloons described in conjunction with FIGS. 4 and 5. For example, a low volume syringe may be coupled to fluid supply tubes 80 (FIG. 4) and 96 (FIG. 5) for injecting fluid to expand the respective balloons. The volume of the injected medium may be controlled by means of a indicator integral with the syringe wherein the volume of injected medium directly corresponds to the expansion of the outer diameter of the balloon. A pressure valve, also integral with the syringe, may be employed to measure the pressure of the balloons, and automatically limit the expansion of the balloons so as to prevent over-stretching of the artery wall, which may lead to serious damage to the intimal lining. Such a volume control mechanism is most useful for balloons made of compliant material. For shunts having two supply tubes (one for each balloon), a syringe having an independent supply line, indictor and valve mechanisms for each fluid supply tube may be sued. Alternatively, pressure-sensitive indicator may be used to control the expansion of the balloons. This type of mechanism may be more suitable for lower compliance balloons wherein the rate of expansion is more pressure-controlled.

Figure 6:
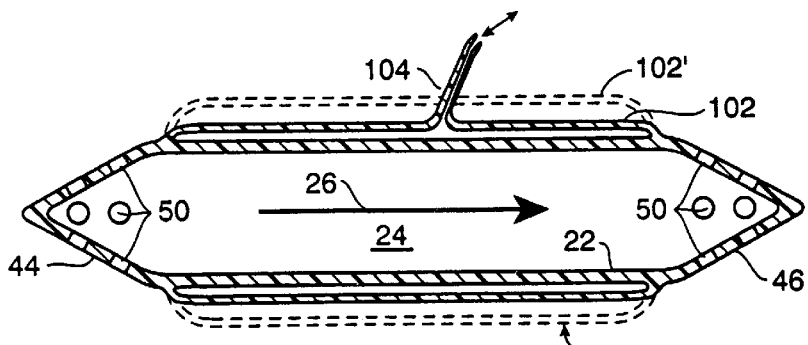

FIG. 6 depicts a shunt 100 generally formed in the manner of the FIG. 4 shunt 70, wherein however the spaced-apart dual balloon configuration is replaced with a single axially extending cylindrical balloon 102 angularly formed about the exterior cylindrical wall of generally the central member 22. A fluid supply tube 104 (or tubes) is formed in communication with an annular chamber formed by the single balloon 102 and the central member exterior wall, to supply or extract the fluid to respectively expand or contract the balloon on demand. The expanded balloon is depicted in phantom line at 102. As previously discussed relative to FIGS. 5 and 4, the single balloon 102 configuration may be formed as a separate single balloon assembly in the form of a tube-like structure which can be coaxially slid over a pre-formed shunt and bonded, glued, etc., thereto to define the balloon chamber.

Figure 7:
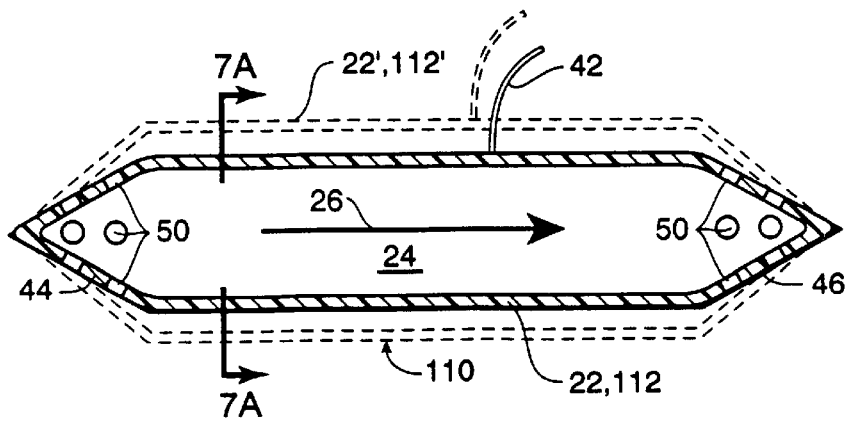
FIG. 7 is an elevational view, in cross-section, of still a further alternative embodiment of the present invention wherein the central member and tapered ends of the shunt are contractible and expandable.
Figure 7A:
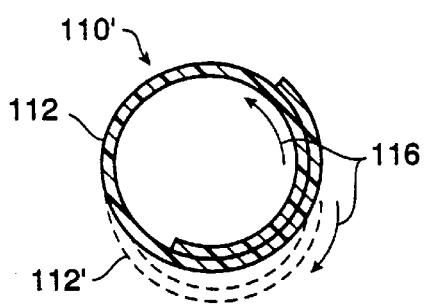
FIG. 7A is a cross-sectional view taken along section line 7A of FIG. 7.

FIG. 7 depicts another embodiment of the invention comprising a shunt 110 formed of a material which is suitably expandable upon demand in response to an inherent property and a stimulus which energizes such property. In this embodiment, the central member and, to some extent, the end members themselves expand to fit snugly within the artery. Such a material may include, for example, the hydrophilic polymer of previous discussion which expands in its hydrogel state, such as a hydrophilic polyurethane, a material having an inherent shape-memory property such as a nickel-titanium alloy, or a soft shape-memory thermoplastic that is actuated at body temperature. The shunt 110 may comprise the previously described configuration of a cylindrical central member 22, terminated at either extremity with tapered end members 44, 46. Alternatively, the central member may be formed not in a continuous cylinder, but may instead define a central member 112 formed of a sheet of suitable material such as polyethylene, polyurethane, polyester, etc., rolled into a cylindrical spiral with overlapping edges 114 of the sheet, as depicted in cross-section in FIG. 7A. In the spiral cylindrical configuration, the tapered end members preferably are formed to, or of, the extremities of the central member 112, and likewise may have overlapping edges.

In the expandable cylindrical configuration of FIG. 7, the shunt walls expand radially outward to increase the overall diameter of the shunt on demand such as, for example, after the shunt has been installed in place in the LAD. Depending upon the material, the cylindrical central member 112 may, or may not, be contractible radially inward when removal of the shunt is desired. In the cylindrical spiral configuration of FIG. 7A, the polymer material becomes slippery in the presence of fluids which causes the spiral of material to uncoil as depicted by arrows 116, thereby increasing the overall diameter of the shunt 110 as depicted in phantom line at 112.

Figure 7B:
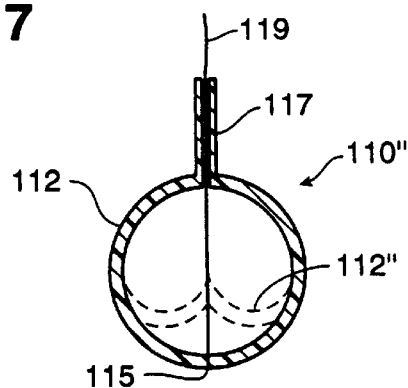
FIG. 7B is a cross-sectional view of an alternative configuration for the shunt of FIG. 7 employing a folding central member.

FIG. 7B depicts an alternative configuration for providing a contractible/expandable shunt 110 employing a polymer material and a wire 115 embedded in the central member 112 along its length. A choker tube 117 is attached to a mid point of the member 112 diametrically opposite to a mid point of the wire 115. A thread 119 attached to the wire mid point extends through the choker tube 117. The application of a pulling force on the thread 119 while holding the tube 117, causes the bottom length of the shunt to fold in as depicted in phantom line at 112 of FIG. 7B. This decreases the dimension of the cross-section of the diameter shunt to facilitate insertion into the arteriotomy or removal from the artery.

Figure 8:
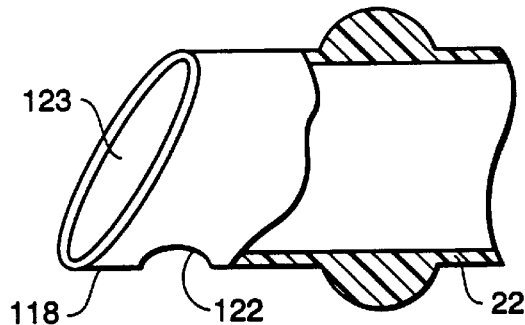
FIGS. 8 and 9 are partial elevational views, generally in cross-section, of alternative tapered end configurations which may be used in the shunts described herein.
Figure 9:
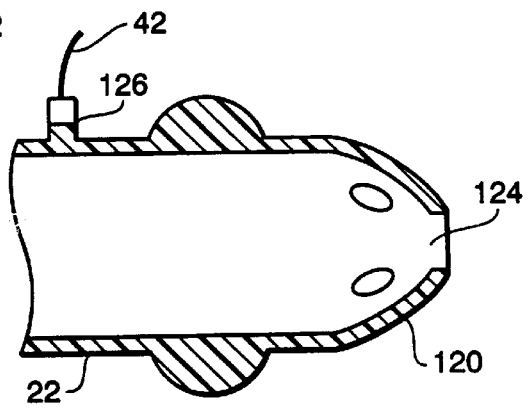

FIGS. 8 and 9 depict alternative configurations for the end members, sharing specifically tapered end members 118, 120, respectively, which may be used with the shunts described herein in place of the more pointed end members 44, 46 of previous description. The end member 118 is sliced preferably at an angle of the order of from 30 to 60 degrees relative to the axial length of the central member 22, and a perforation or opening 122 of selected size may be formed in the wall of the end member generally coincident with the extended point of the end member 118. The resulting tapered end of the end member 118 may be formed to curl radially inward around the oval circumference thereof to provide a more rounded end while further decreasing the size of a central opening 123.

The tapered end member 120 of FIG. 9 is shortened in length with a relatively acute taper and a central opening 124. The shortened end member 120 facilitates insertion of a shunt in an incision where the opposite end of the shunt is inserted initially, since the shortened end member 120 more readily clears the respective end of the incision. The FIG. 9 further depicts an integral stub 126 formed of the shunt material at a location approaching an extremity of the central member 22. The stub 126 provides a readily grasped portion of the shunt to facilitate the insertion of the shunt via forceps. The stub may include connection for the filamentary strand 42 as shown. As will be readily appreciated by those of skill in the art, although the various embodiment of the invention are described in a symmetrical fashion about the center of the shunt, the ends thereat, and the end members particularly need not be of like configuration and may vary to facilitate the insertion, function, and removal of the device. For example, the end member of the shunt for first insertion into the vessel may have a more blunt end, as the design of the end member 120 of FIG. 9, to avoid inserting the end member 120 into a side branch of the vessel. Alternatively, an end member having a jointed tip distal to the openings or perforations 52 may facilitate easier insertion with a reduced possibility of damage to the vessel. The end of the shunt second inserted may have a finer tip because the second end may necessarily be inserted when the central member 22 is bent during placement in the arteriotomy incision 32.

Figure 10A:
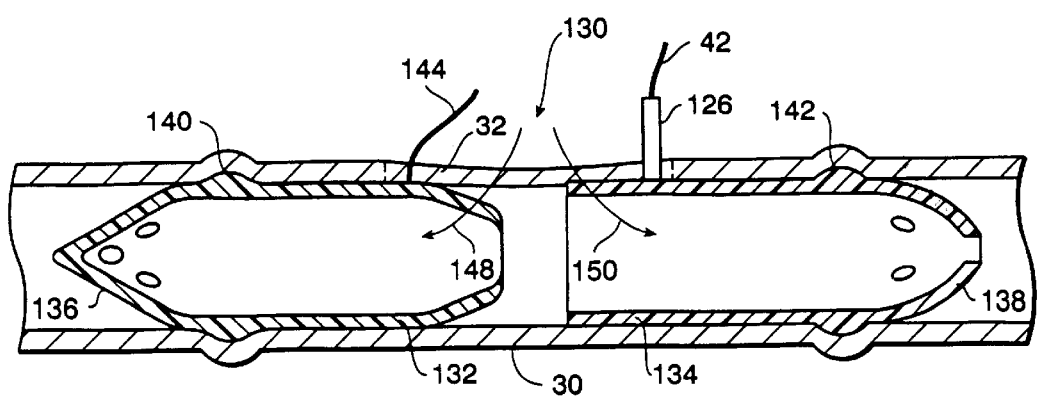
FIGS. 10A, 10B are simplified elevational views of an alternative two-piece embodiment of the invention, further depicting a sequence of steps taken by a surgeon to install the shunt at the anastomosis site.
Figure 10B:
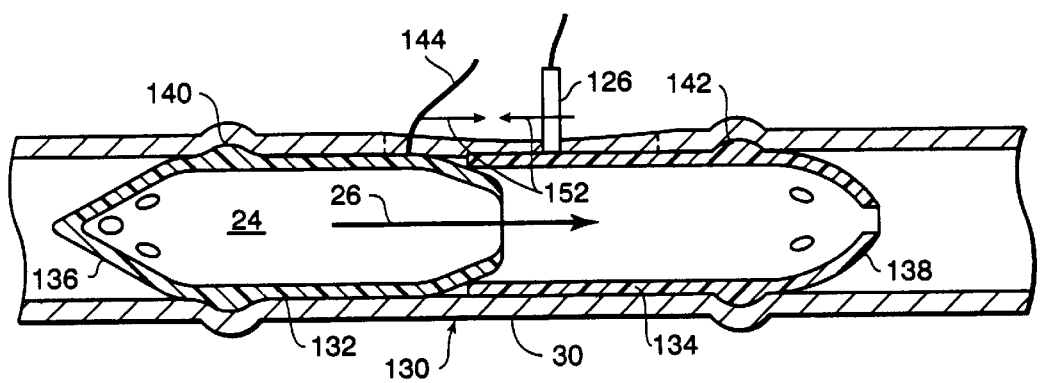

FIGS. 10A, 10B depict an alternative embodiment of a two piece shunt 130 which configuration facilitates the initial insertion of the shunt through the incision 32 and into the LAD 30. The shunt 130 is formed of two shortened central members 132, 134, wherein one central member, for example 132, has a slightly smaller diameter than the confronting central member, for example 134. The member 134 of larger diameter has a leading portion thereof somewhat hardened to facilitate the meshing and thus assembly of the two halves into the single piece shunt 130 (FIG. 10B). The shunt half formed of central member 132 includes a tapered end member 136 formed therewith similar to the more pointed end members 44, 46 of FIGS. 2–4, 6, 7. The shunt half formed of central member 134 includes a tapered end member 138 which resembles that of FIG. 9, but which could be otherwise. In this example, the annular ridges 140, 142 are shown as non-balloon types such as those of FIG. 3, but could comprise the balloon or other configurations of ridges of description herein. Filamentary strand 144 and an integral stub 126 are secured to respective central members 132, 134 respectively.

FIG. 10A depicts the separate insertion of each shunt half, where shunt half 132, 136 is inserted proximally in the LAD 30 using the strand 144 and forceps to urge the half in the direction shown by arrow 148. Then shunt half 134, 138 is inserted distally in the LAD 30 using an integral stub 126 and forceps to urge the half in the direction of arrow 150. Then as depicted in FIG. 10B, the two halves are manipulated to provide the single piece shunt 130 by gently pulling the strand 144 and stub 126, and thus the halves, towards each other as depicted by arrow 152, while guiding the halves with forceps until the halves are united. As may be seen, the distal half of the shunt 130 has the larger diameter such that the blood flow in the artery passes unobstructed from the smaller, inside diameter to the larger outside diameter in the joined region.

Figure 11A:
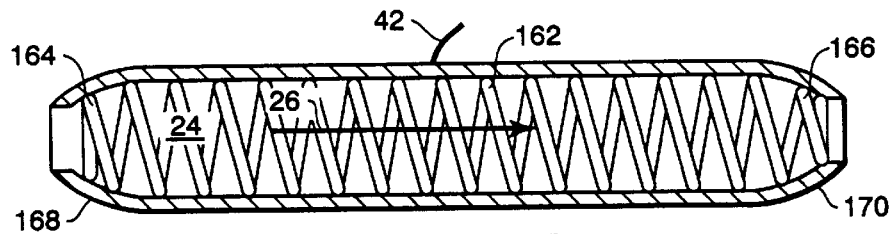
FIG. 11A is an elevational view, in cross-section, of a further alternative embodiment of the invention employing a very flexible coil coated with a flexible material such as silicon, latex, etc.
Figure 11B:
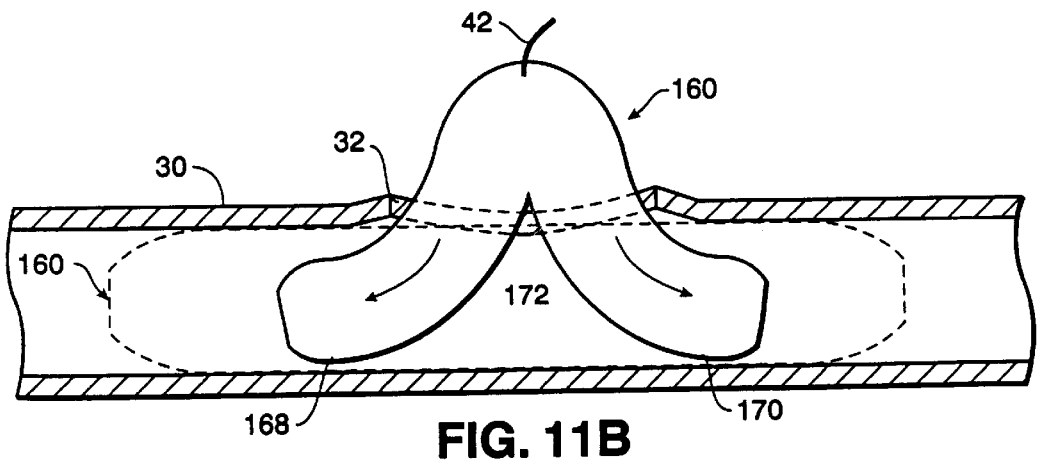
FIG. 11B is an elevational view illustrating a procedure for inserting the shunt of FIG. 11A in place in an artery via an incision.

FIGS. 11A, 11B depict a further alternative shunt 160 formed of a lightweight flexible coil 162 formed of, for example, a stainless steel filament. In this embodiment, substantially the entire structural support means of the device is provided by the lightweight flexible coil 162. As shown in FIG. 11A, the coil 162 may be wound having a substantially uniform diameter along the length of the central member. The dimensions of the spiral of the coil 162 may also be varied to provide the expanded or tapered end members as described in other embodiments of the invention. To selectively alter the dimensions of the coil 162, the wire of the coil 162 is would around a mandrel having the desired dimension of the coil. Thus, expanded end members, i.e., end members having a smaller diameter than the central member, (not shown), may be formed by wrapping the wire of the coil 162 around a suitably shaped mandrel. With each possible configuration for the central member and end members, the spiral of the coil 162 preferably is tightened at the ends 164, 166 thereof to provide decreasing diameters and thus tapered end members 168, 170 for facilitating insertion in the artery 30. The coil 162 is coated with a flexible material such as, for example, silicon, to define an impervious tube having a lumen 24 therethrough. Alternatively, the coating would be interrupted to provide perfusion holes in a portion of the lumen 24. The resulting shunt is very flexible and is configured with an outside diameter which allows it to fit snugly within a blood vessel such as the LAD 30 while maintaining blood flow through the lumen. The wire of which coil 162 is comprised is shown as a round wire in these exampled, but may be flat or have other configurations as desired. FIG. 11B depicts one manner of installing the shunt in the LAD 30, wherein the end members 168, 170 are pinched towards one another, either separately or simultaneously, passed through the incision 32, and then urged into respective proximal and distal portions of the LAD as shown by arrows 172, using the filamentary strand 42 and forceps. In FIG. 11B the central member of the coil shunt 160 is depicted in place within the LAD 30 in phantom line. As noted above, the central member comprised of a coil shunt may be used separately or may be joined with other features of the invention as described herein such as the end members of FIGS. 8–9, the lumen of FIGS. 4, 6, 7, etc.

Figure 12A:
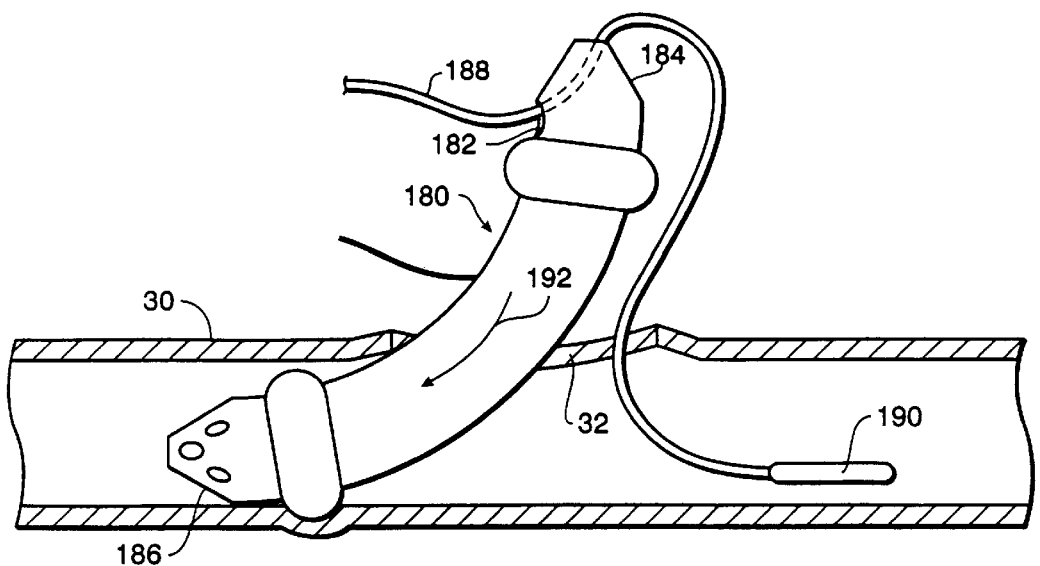
FIGS. 12A, 12B are elevational views, in partial cross-section, of a modified embodiment of the invention, illustrating a procedure for inserting the shunt in place in an artery via an incision.
Figure 12B:
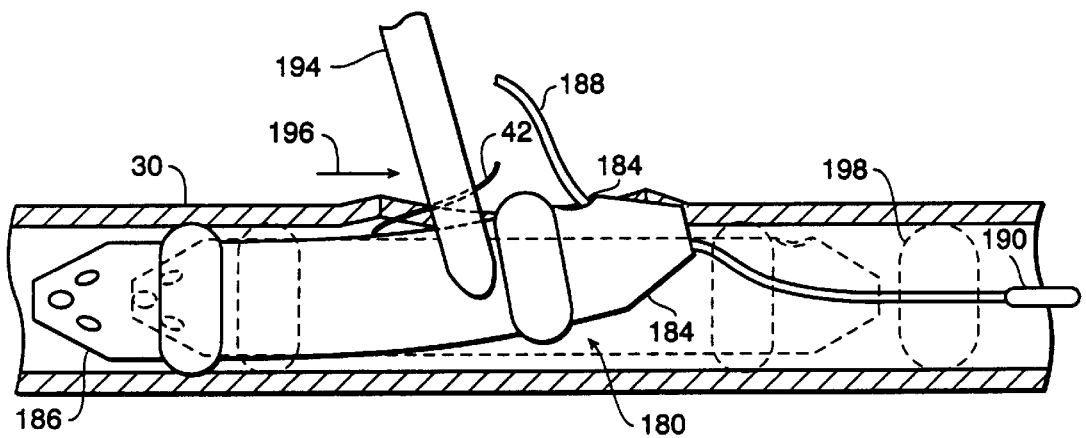

FIGS. 12A, 12B depict a further modification to a shunt or shunts of previous or following description, which modification lends itself to an alternative technique for insertion of a shunt 180 in place in a blood vessel such as the LAD 30. The shunt 180 is modified to include a means for attaching a guide such as a guide wire or catheter at a point on the shunt such as a perforation 182 formed in the distal end member 184. The perforation 182 is adapted to receive a flexible guide wire 188 such as those used for catheters. The guide wire may include a typical helical coil 190 at the tip thereof or may include a balloon device as discussed below. Where the device is inserted through an incision such as arteriotomy 33 insertion of the shunt 180 is initiated as in FIG. 12A by inserting a proximal tapered end member 186 into the LAD 30 and urging the shunt as depicted by arrow 192 by gently pulling on the filamentary strand 42 while guiding and urging the shunt with forceps (not shown). The guide wire 188 is passed through the perforation 182 and thence through the incision 32 and distally into the LAD 30. As next depicted in FIG. 12B, the guide wire 188 then is used to guide the distal end member 184, into the LAD 30 while the shunt 180 is urged distally with forceps 194 and the strand 42, as depicted by arrow 196. After the shunt 180 is in place, as depicted in phantom line, the guide wire 188 is removed and the anastomosis construction can proceed. To prevent the guide wire 188 from being dislodged from its position distally in the LAD 30, a balloon device 198 typically employed with catheters may be employed at the end of the guide wire. Expansion of the balloon device 198 as depicted in phantom line secures the end of the guide wire 188 to prevent it from being dislodged while the shunt is being urged distally along the guide wire.

Where the shunt is positioned using a catheter (not shown) which passes through the interior of the vessel 30, the shunt is preferably affixed at one end to the most distal end of a catheter and advanced along with the catheter through the interior of the vessel 30 until the shunt reaches the point at the interior of the vessel 30 where the incision will be made to form the arteriotomy 32.

Figure 13A:
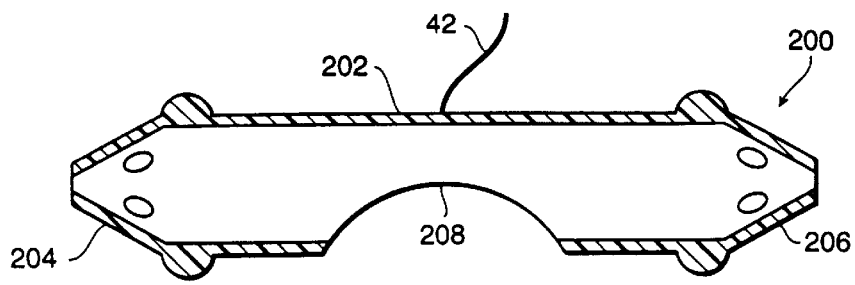
FIGS. 13A, 13B, 13C are elevational views, in cross-section, of a further modified embodiment of the invention, further illustrating a procedure for inserting the shunt in place in an artery via an incision.
Figure 13B:
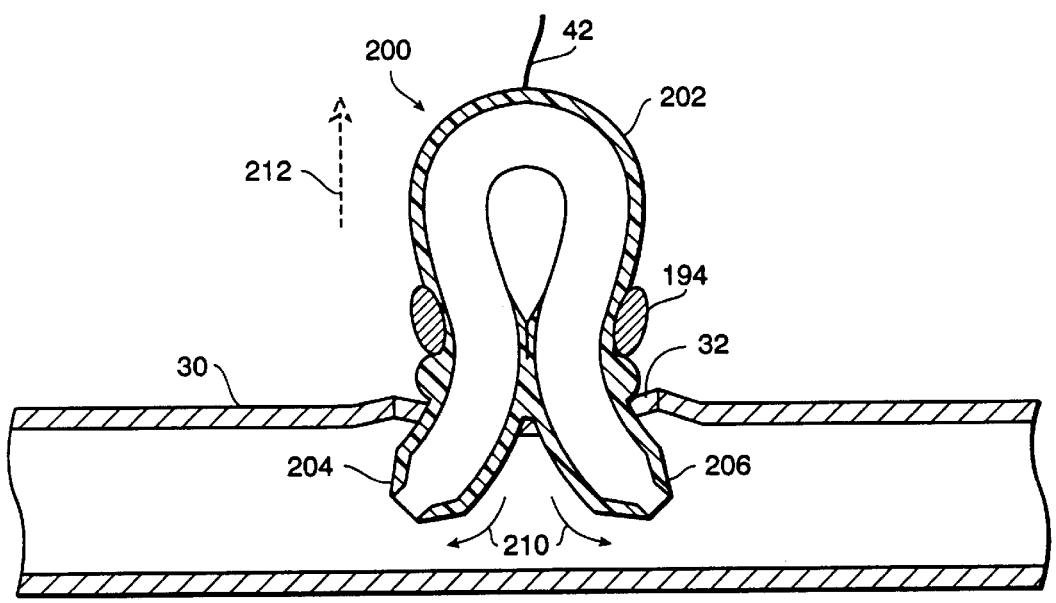
Figure 13C:
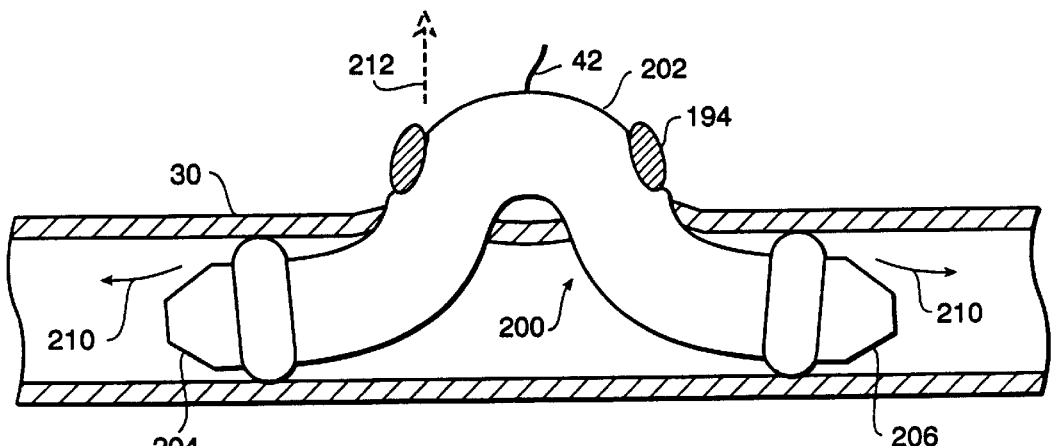

FIGS. 13A, 13B, 13C depict still another alternative embodiment of the invention and a preferred method of installation of a corresponding shunt 200 via the incision 32 of, for example, the LAD 30. The shunt 200 may be formed generally of one of the various shunt configurations of previous description with a central member 202 and tapered end members 204, 206. However, as depicted in FIG. 13A, the shunt 200 is modified by removing an arcuate portion from the central member 202 to define a necked-down section 208 along a substantial length of the central member 202, as shown. The arcuate portion which is removed may be of different lengths and/or depths into the central member, as desired. The necked-down section 208 enhances the bending flexibility of the shunt 200, which configuration thus lends itself to a preferred method of installation of the shunt 200. To this end, referring to FIG. 13B, the shunt 200 may be folded at its middle in the direction of the necked-down section 208, and then pinched together as with the forceps 194 or other instrument of FIG. 12B, shown here in cross-section. The tapered end members 204, 206, in their pinched-together configuration, are inserted through the incision 32 and urged in respective proximal and distal directions in to the LAD 30, as depicted by arrows 210. Further gentle manipulation of the shunt 200 is made with the forceps 194 in successive stages until the shunt is in a position such as shown in FIG. 13C where each end member 204, 206 is fully aligned coaxially in the LAD 30. The shunt 200 then gently is reciprocated while being pushed down via the forceps into full alignment within the LAD 30, as shown in previous figures. Upon conclusion of the suturing process but prior to tightening the suture loops, the modified shunt 200 is readily removed by pulling gently on the filamentary strand 42 to raise the necked-out and thus flexible central member 202 sufficiently to enable the surgeon to grasp, and thus pinch together, the shunt via the forceps 194. Initial and subsequent movement of the shunt 200 also is depicted by FIGS. 13C, 13B, respectively, if the previous insertion steps of arrows 210 are reversed as depicted by arrow 212, shown in phantom line.

Figure 14A:
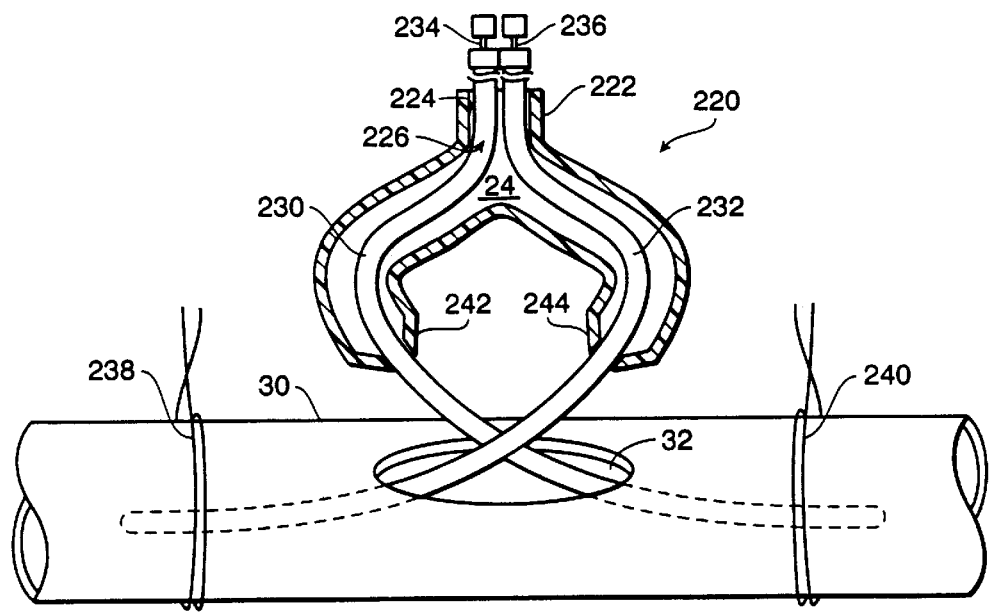
FIGS. 14A, 14B, 14C are elevational views, in partial cross-section, of a further alternative embodiment of the invention, further illustrating a procedure and associated implements for inserting the shunt in place.
Figure 14B:
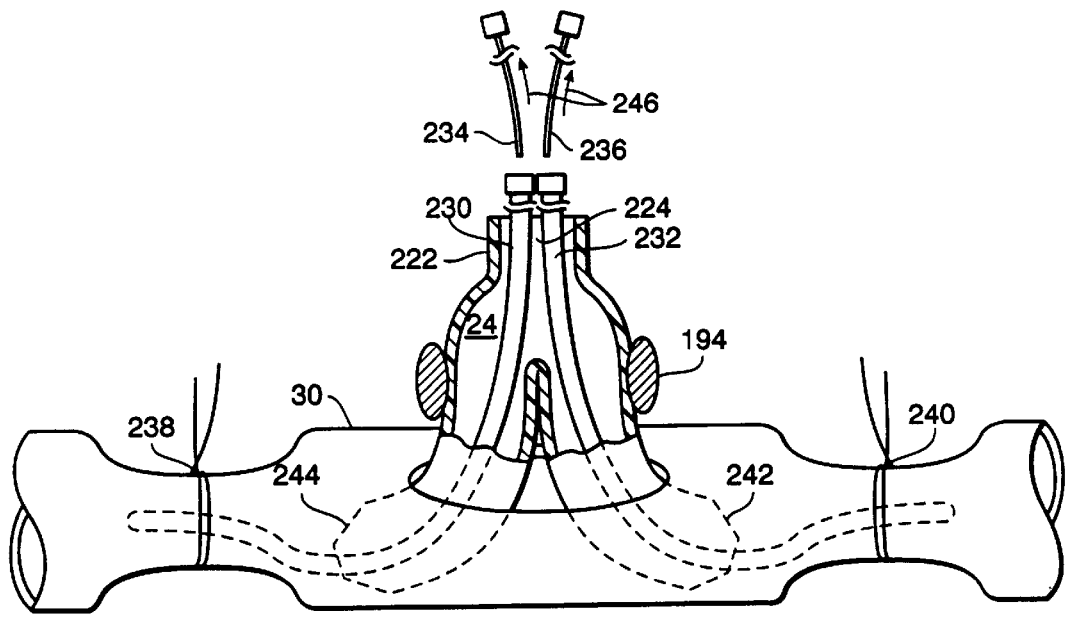
Figure 14C:
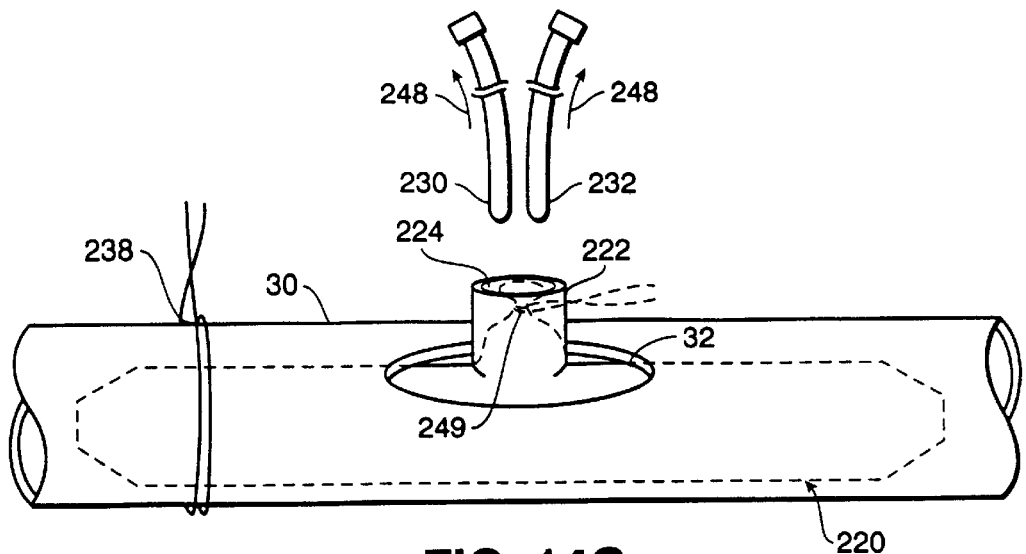

FIGS. 14A, 14B, 14C depict yet another alternative embodiment of the invention and another associated method of installation of a corresponding shunt 220 in place in an artery such as the LAD 30. The shunt 220, as in FIGS. 13A–13C, in general may comprise one of the shunt configurations of previous description formed of similar material. However, the shunt 220 is modified to include a shunt access member 222 which may be oval in cross-section to generally match the shape of the arteriotomy during the anastomosis construction and which provides an access lumen 224 in communication with the lumen 24 of the shunt 220.

The combination of the lumen 24 and the access lumen 224 creates a substantially T-shaped fluid communication pathway such that blood can be removed from the vessel for analysis or surgical purposes. Alternatively, intravenous fluids, medicines, etc. can be introduced into the vessel via access lumen 224 to allow pharmaceutical intervention at the site of the anastomosis or distally by virtue of the distal perfusion enabled by the device of the invention. The configuration of the shunt 220 is illustrated in FIG. 14C installed in place in an artery such as the LAD 30. The shunt configuration employing the shunt access member 222 enables an installation procedure utilizing a pair of introducers 226, 228 which aid in guiding the shunt 220 into place in the LAD 30. The introducers are generally similar to dilators used in bypass procedures. In particular, the introducers 226, 228 each include a very flexible, or floppy, tube 230, 232 of, for example, a polymer material. A guide wire 234, 236 of selected firmer flexibility is threaded into respective floppy tubes 230, 232 to provide initial support for the tubes, to facilitate the shunt installation, described below.

FIG. 14A illustrates initial steps in the procedure of installing the shunt 220. A first step typically is to install proximal and distal snares 238, 240 loosely about the LAD 30 at locations proximal and distal to the arteriotomy or incision 32. The introducers 226, 228 are each threaded through the shunt access member 222, out through respective tapered end members 242, 244, and thence into the LAD 30 via respective distal and proximal apexes of the arteriotomy 32. As illustrated in FIG. 14A, the end of the introducer 226 is fed through the distal snare 240 while the end of the introducer 228 is fed through the proximal snare 238. FIG. 14A depicts the shunt 220 after initial steps of urging the shunt towards the incision 32 along the introducers 226, 228, wherein the tapered end members 242, 244 are forced to begin converging together as they are urged along the guiding introducers.

As shown in FIG. 14B, the snares 238, 240 are tightened before the installation procedure is continued, to secure the introducers in place in the LAD 30. The support wires 234, 236 then are removed from within the respective floppy tubes 230, 232 as depicted by arrows 246, to provide increased flexibility in rotating the shunt 220 while urging the end members 242, 244 into the LAD 30. Forceps 194 or other appropriate instruments are employed to aid in pinching the ends of the shunt 220 together to facilitate their entry through the arteriotomy, as shown in FIG. 14B. The procedure is continued until the shunt 220 is in place in the LAD 30, as depicted in partial phantom line in FIG. 14C. The snares 238, 240 are removed and the floppy tubes 230, 232 are removed from the shunt as shown by arrows 248. Alternatively, the snares can be retightened around the shunt as depicted by 238 in FIG. 14C to secure an adequate blood seal for the anastomosis. In one procedure, the shunt access member 222 is ligated with a suture 249, or with a filamentary strand previously secured about the member 222.

Alternatively, the shunt access member 222 may be replaced by an IMA supporting member such as that shown in FIG. 16. The distal end of the IMA then is slipped over the IMA supporting member which, together with the shunt 220, provides support for the anastomosis construction.

Although a pair of introducers are depicted in performing the installation procedure of FIGS. 14A–14C, a single introducer may be employed with an installation procedure generally similar to that described relative to FIGS. 12A–12B. That is, an introducer is threaded through the shunt access member 222, out one end member of the shunt and into the LAD 30. Then installation is accomplished by first inserting the free end of the shunt into the LAD opposite to the location of the end of the introducer, whereupon the introducer then is used along with forceps to finish the installation as in FIGS. 12A, 12B.

In addition, the ends of the single or dual introducers may include an inflatable balloon device such as balloon device 198 discussed relative to the guide wire 188 of FIG. 12B, to secure the introducer in place within the LAD 30. Thus, the snares 238, 240 may be dispensed with which reduces the arterial trauma which can occur from the pinching effect of the snare. Further, means other than a suture or strand may be employed to seal the shunt access member 222. For example, surgical clips or an expandable material such as the hydrogel material of previous mention, may be used.

Figure 15A:
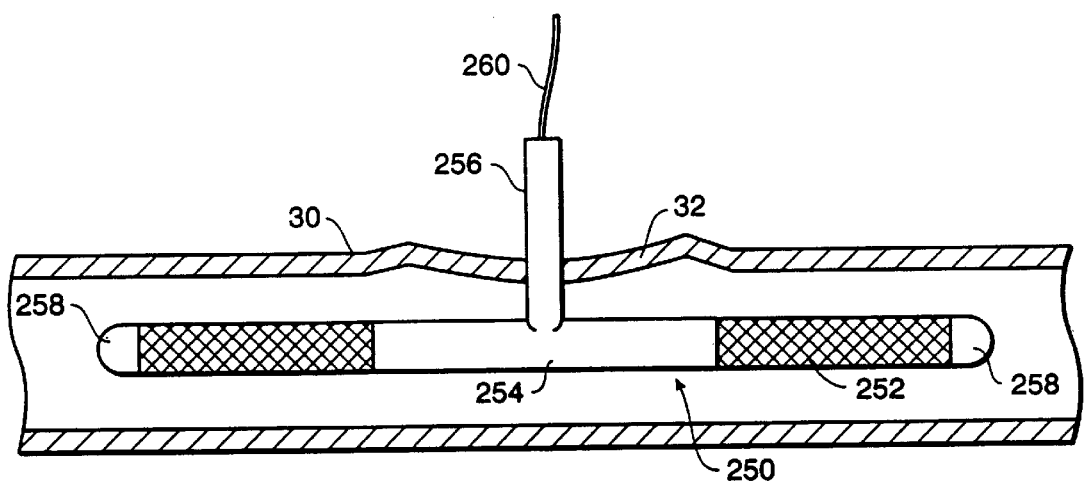
FIGS. 15A, 15B and 16A, 16B are elevational views of still other alternative embodiments of the invention employing a braided tube and a laminated foil structure, respectively.
Figure 15B:
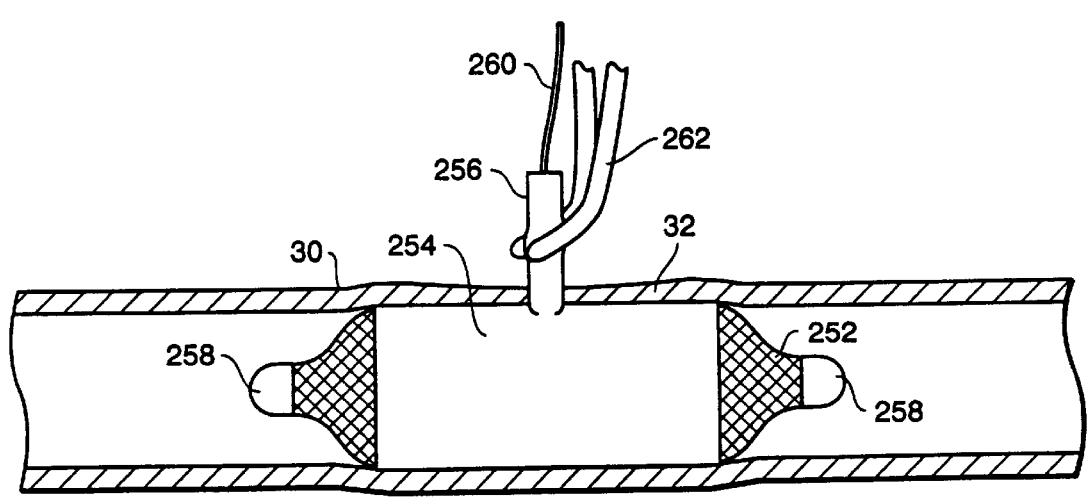

FIGS. 15A, 15B depict a further embodiment of the invention employing a braided tube 252 to form the central member and tapered end members of a shunt 250. A central portion 254 of the braided tube 252 is coated with an elastomer material to provide an impermeable membrane that stretches when the braided tube 252, that is, the shunt 250, is compressed axially. The remaining uncoated end portions of the braided tube 252 provide the tapered end members of previous description as well as the openings to allow the flow of blood through the shunt. A choker tube 256 is integrally secured to a mid point of the central portion 254 of the shunt. Atraumatic tips 258 of soft elastomer or plastic material are formed as end members at the ends of the braided tube 252 to prevent damage to the artery during insertion. A thread 260 is secured to each end of the shunt and thence through the lumen of the central portion and out through the choker tube 256.

The shunt 250 is inserted through the arteriotomy or incision 32 by slipping first one end and then the other therethrough into the LAD 30, as depicted in FIG. 15A. As depicted in FIG. 15B, the shunt 250 is expanded radially outward to engage the interior wall of the LAD 30, by applying a pulling force to the thread 260 while holding the choker tube 256 to compress the braided tube 252 axially. The expanded central portion 254 spans, and thus occludes, the arteriotomy. The shunt is maintained in the expanded condition by pinching the choker tube 256 with locking forceps 262 or other pinching device, to lock the thread 260 therein.

Figure 16B:
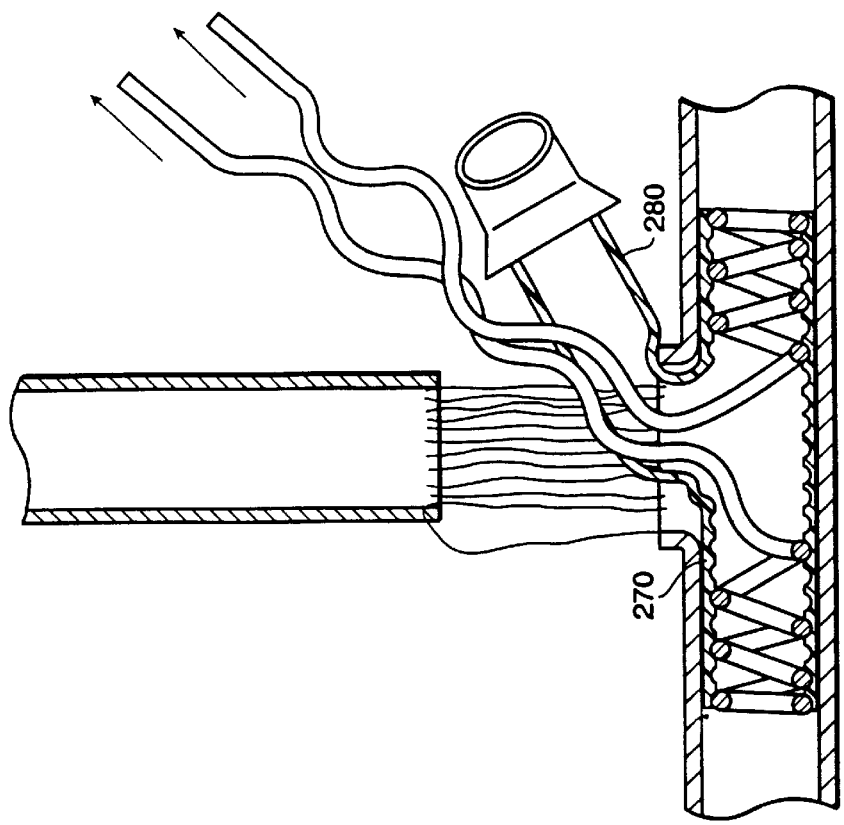
Figure 16A:
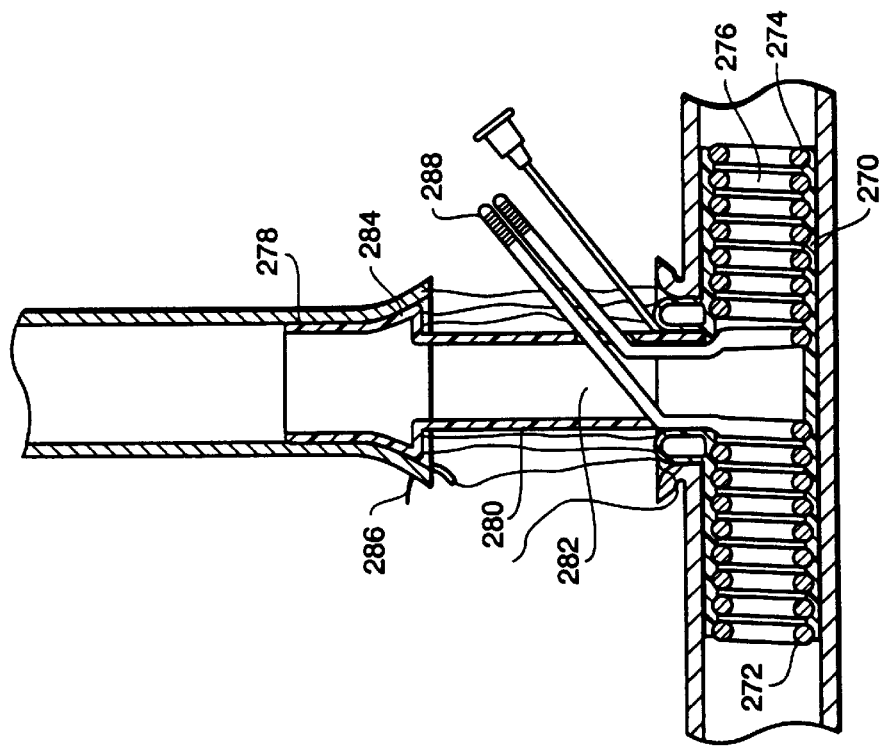

FIGS. 16A, 16B depict still a further embodiment of the invention wherein a coil shunt 270 is formed of a pair of coils 272, 274 which are laminated with an elastomer material to provide flexible tubular members about the coils. The elastomer material may also extend between the coils 272, 274 to define a tubular center member 276. The center member 276 is formed about and between the coils by means of, for example, a conventional molding process and may include, in the region of the anastomosis, an inflatable, generally oval shaped balloon device 278 which when inflated exposes the edges of the incision 32 to facilitate the suturing procedure. An IMA supporting member 280 formed of an elastomer material and having a lumen 282 therethrough, is molded at its distal end to the elastomer material extending between the coils 272, 274. The resulting IMA lumen 282 thus is in communication with the lumen 24 of the shunt 270 to allow the flow of blood from the IMA 38 to the LAD 30 if desired. However, the combined shunt structure, including the inflatable balloon device 278, maintain a dry anastomosis site. In addition, the IMA supporting member 280 may include at its proximal end an enlarged flange 284, formed of material such as hydrogel or an inflatable balloon, which exposes the distal end of the IMA 38 to further facilitate the suturing procedure. To illustrate, FIG. 16A depicts a suturing needle 286 used in a typical suturing procedure, wherein the procedure is aided by the exposure of the anastomosis by the IMA flange 284 and the balloon device 278 as depicted.

As show in FIGS. 16A, 16B, the proximate ends of the coils 242, 244 are accessible via coil removers 288 whereby the coils may be unraveled independently from within the laminated elastomer material, FIG. 16B, to provide an enlarged lumen 24 or to facilitate the removal of the shunt 270.

It is understood that an IMA supporting tube, such as the tube 280 of FIGS. 16A, 16B, may be employed in the various shunt configurations of description herein if desired, and is not limited to use with the coil configuration as shown and described. Alternatively, the central tube 280 can be connected to other source arteries or veins to provide perfusion and allow drug delivery. These source arteries can be the femoral vein, aorta, medial artery, etc. Alternatively, the T-shaped shunt or standard shunt can be used to provide intermediate blood perfusion to the distal myocardium for cases when the patient is hemodynamically unstable during the operation without necessarily focussing on occlusion. The goal would be to prevent further ischemia damage and to stabilize the patient before beginning an anastomosis.

Figure 17:
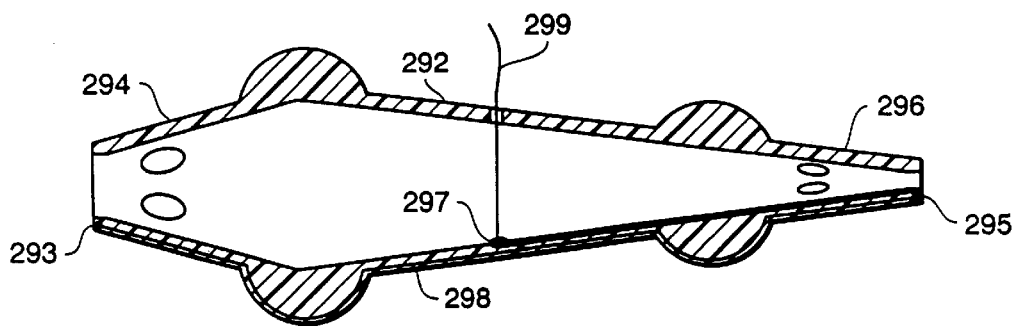
FIG. 17 is an elevational view, in cross-section, of an asymmetrical shunt configuration, further depicting a gum wrapper thread technique for facilitating shunt removal.

FIG. 17 depicts further alternative modifications to the various shunt configurations described herein, in accordance with the aspect of the invention where an asymmetric construction is used. For example, a central member 292 and associated tapered end members 294, 296 may be formed with slightly tapered geometry to define thus an asymmetrical shunt configuration matching the typical decreasing diameter of a coronary artery in the distal direction. In addition, a shunt may include a means for splitting the shunt, either axially along its length of circumferentially, to enhance the collapse of the shunts diameter to facilitate its removal. To this end, in FIG. 17, a thread 298, flexible wire, etc., is embedded within the wall of the shunt, preferably at least along the central member 292 in the same manner as a gum wrapper package is provided with a filament to split the package wall. The thread 298 may extend from a point 293 along the length of the shunt to a point 295, and thence in a loose loop to a tear patch 297. The thread then extends from the shunt as depicted at 299 through, for example, a suitable opening in the diametrically opposed wall of the central member 292. Thus the thread 298 is used as the means for aiding the insertion of the shunt where gentle pulling does not tear the patch 297 to initiate the splitting action. When the shunt is to be removed, forceps or other appropriate instruments are placed against the shunt and a greater pulling force is applied to tear the patch 297 and cause the thread 298 to slice through the shunt wall.

As noted above, the various embodiments described herein may be asymmetrical in design and construction. This extends to the tensile strength of the overall device and to the central member 292 particular. Because one end member of the device is typically introduced first, the central member may have various degrees of stiffness along its length. Preferably, the end designed for first insertion is stiffer to allow the first end to be pushed into the vessel and to avoid undesired flexing of the central member 292 upon insertion. The opposite end designed for second insertion, is more flexible so that it may be more readily bent for insertion when the first end is already in place in the vessel. Having a more flexible section also provides ease of removal at the end of the anastomosis procedure.

Similarly, although in the embodiments described herein and shown in the attached figures the central member is generally centrally disposed relative to the circumference of the end members, the central member may be offset such that the shunt device could be positioned within the arteriotomy such that the central member would lie closely along the inner side of the vessel opposite the site of the arteriotomy incision. This configuration maintains the structural portion of the shunt device, which actually rests inside the vessel, out of the way of the suturing procedure whereby the surgeon attaches the vessel to complete the anastomosis.

Figure 18:
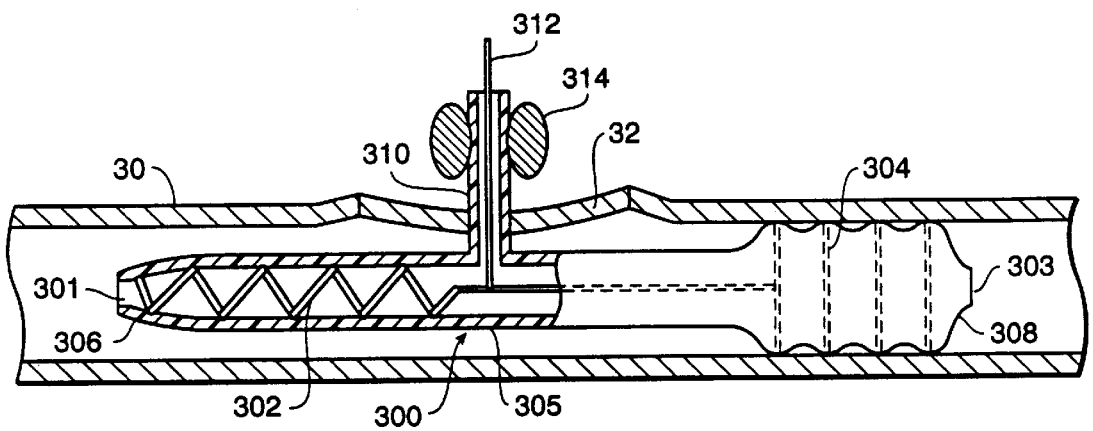
FIG. 18 is an elevational view of yet another alternative embodiment of the invention employing an expanding spring structure.

FIG. 18 depicts a further alternative embodiment of the invention, wherein a further coil structure is employed in a shunt 300. More particularly, thin, flexible wire springs or coils 302, 304 are laminated with a coating of a flexible elastomer material, generally as previously depicted in FIGS. 16A, 16B, to form an impervious central member 305 and generally tapered end members 306, 308. The end members are formed with openings 301, 303. A choker tube 310 is formed with a wall of the central member 304 at generally a midpoint and extends generally normal therefrom. Threads are secured to respective facing ends of the coils 302, 304, are passed through the choker tube 310 as divided threads and extend from the tube as a united thread 312. As depicted in solid, a pulling force applied to the thread 312 while the choker tube 310 is held axially stretches the coils (herein only coil 302 and laminated coating is shown in a stretched condition). A locking forceps 314 is used to pinch the choker tube 310 against the thread 312 and to maintain the coils and thus the shunt in the extended condition. The small diameter of the unextended shunt 300 allows ready insertion in the artery. Once in place, the forceps 314 are removed and the coils 302, 304 return to their natural axially compact state (herein shown by the coil 304 and laminated coating, in phantom line). As may be seen, when the coils 302, 304 return to their natural state, the diameters of the shunt 300 at either end expand radially outward to provide snug engagement of the elastomer coating with the interior walls of the LAD 30 proximal and distal to the anastomosis site.

Figure 19:
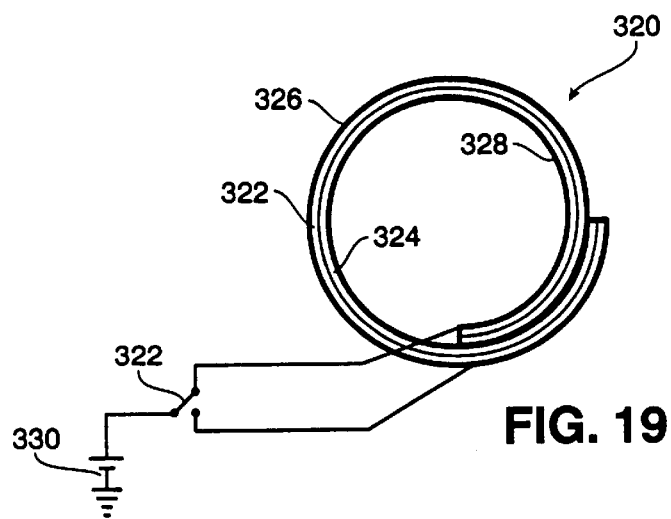
FIG. 19 is a cross-sectional view of another alternative embodiment of the invention.

FIG. 19 depicts a further alternative embodiment of an expandable shunt 320 wherein a cylindrical unfolding spiral is formed of two bonded sheets 322, 324 of, for example, a nickel-titanium alloy material having an inherent shape-memory property. One sheet, for example 324, is annealed in the shape of a tightly curled cylinder, while the other sheet, for example 322, is annealed as a flat or less curled sheet. A heating coil 326, 328 is bonded to respective sheets 322, 324. The shunt 320 is formed of the bonded sheets rolled into a spiral cylinder of a diameter corresponding to the desired diameter in use. Since the shunt 320 is expandable through most sizes of arteries, the initial diameter of the shunt may be made smaller than the diameter of the smallest arteries. Application of a small electrical current for a short duration to the coil 328 bonded to the tightly curled sheet 324 via, for example, a voltage source 330 and a switch 332, causes the sheet to contract, facilitating the insertion of the shunt 320 in the artery 30. Upon insertion of the shunt, another small electrical current is applied for a short duration to the coil 326 of the sheet 322 which is annealed while flat or less curled, causing the cylindrical spiral to unfold to expand the diameter of the shunt. When contraction of the shunt 320 is desired as when the shunt is to be removed, the current is applied to the coil 328 which causes the cylindrical spiral to contract radially inward.

Referring to FIG. 20, an embodiment of the invention has a selectively expandable members 350 disposed proximate to each end member 351 and proximal to the openings/perforations 352 for perfusion. Each end member 351 has a tip 353, distal to the perfusion openings 352, pointing in opposite directions respectively and generally coaxial with the central member 354. As shown in FIG. 20, the shunt device has been inserted through arteriotomy 355 formed in vessel 30 and has been positioned such that each expandable member 350 is maintained in a position beyond the apex of the incision forming the arteriotomy 355 and is placed prior to selective expansion at the expandable member(s) 350. In this embodiment, each expandable member 350 is an annular section of expandable foam that is covered with sheath means 356 to maintain the expandable member 350 in an unexpanded state until the placement and positioning of the shunt is complete. In the embodiment of FIG. 20, each sheath means 356 is attached to a thread 357 for selective removal of the sheath means 356 from about the expandable members 350. The thread 357 may be a single line which approaches the central member 354 at approximately the mid-point or may be offset, or may have several individual threads, at least one of which is attached to each sheath means and which are interwoven. Thread guides 358 may direct each thread axially along the central member 354 to attach to the sheath means 356. FIG. 21 shows the relative configurations of the device having one expandable member 350 in an expanded state and one expandable member 350 remaining in an unexpanded state.

The thread guides 358 may be rigid plastic fixtures integrally formed with the central member 354 or may be provided by a plurality of annular plastic bands (not shown) which tightly surround the central member 354. In this configuration, threads 357 pass underneath the annular bands and are connected to the sheath means 356. Ideally at least two annular bands are provided in a similar fashion to the embodiment shown in FIG. 22, i.e., one each between the point where a thread or threads 357 engage to shunt device and where a thread 357 is attached to the sheath means 356. Thus, when the sheath means are removed by drawing tension on the threads 357, the sheath means 356 are tightly gathered and collected next to the annular bands such that the sheath means 356 do not become detached from the device and remain securely attached to the central member 354 while the surgical procedure is completed.

Referring to the embodiments of FIGS. 21 through 23C, the central member 354 preferably has a structural support means comprised of a coil 272 to provide a coil-reinforced lumen that provides flexibility without kinking and reduces the overall thickness required for the lumen wall. The coil 272 may be continuous, may have a variable winding frequency, and may also be a square, flat, or triangular shape. For ease of insertion and removal, the coil 272 may be provided in individual segments that have interruptions at one or more points along the length of the central member 354. Preferably, the interruptions are near the center of the central member 354, for ready removal for example, at the point at which the central member 354 of the device is affixed to the thread 362.

FIG. 22 shows the embodiment of FIG. 20 after the sheath means 356 have been removed from about the expandable members 350 and drawn towards the center of the shunt by exerting tension on the thread 357 via thread guides 358. In this configuration, the sheath means 356 are gathered together by the thread 357 when removed from about the expandable members 350 to avoid becoming entangled during the anastomosis procedure. The expandable members 350 expand to contact, in annular fashion, the interior at the vessel 30 to seal the flow of blood to prevent leakage through the arteriotomy 355 while establishing flow into and out of the perfusion holes or perforations 352, through the central member 354, and out the opposite perfusion holes to provide perfusion distal to the arteriotomy.

Selective expansion may also be provided by a thread 357 which actuates a mechanical means (not shown) for causing the means for providing an enlarged diameter to expand. For example, a proximal collar may be provided having a plurality of outwardly bendable wires or tires that bend outward when tension is exerted on a thread attached to the distal end of the mechanical means. Thus, as tension is drawn on the distal end of the mechanical means, the proximal collar remains in place while the wires or tires bend radially outward forcing a permanent sheath means 356 or other covering to engage the inside of the vessel.

Each of the embodiments of the distal perfusion device (shunt) having expandable members may readily be provided by polyvinyl acetate or polyvinyl alcohol foam particularly annular foam sections that are close to or about the end members of the shunt. The rate of expansion if the expandable members may be altered by coating the foam with a hydrophilic or coating that provides lubrication. The coating also aids atraumatic insertion and removal of the shunt and means are not used, facilitates removal of sheath means in certain embodiments. The coating may include heparin or other blood-related products compatible for export to dissolution in the blood stream. Particularly where sheath means are not used, the foam may also be treated with a cured adhesive or coating of silicon or a like substance to retard the fluid permeability of the foam, thereby reducing the rate of expansion and providing additional time to position the shunt during the anastomosis procedure prior to expansion.

Figure 23A:
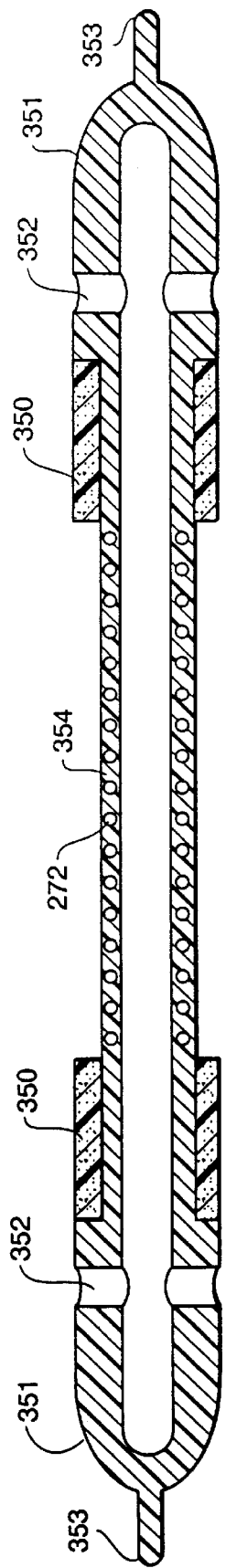
FIGS. 23A through 23C are embodiments of the invention having varying configurations of the expandable members relative to the perfusion openings, and optimally permanent and/or semi-permeable sheath means.

FIG. 23A shows a preferred configuration for the end members 351 being in close conformity with expandable members 350 such that minimal trauma to the vessel results from insertion of the device. In this configuration, the maximum outer diameter of the expandable members 350, in their original state, closely approximates the outer diameter of the end member 351 at the point where the end member 351 and the expandable member 350 meet. The expansion of these expandable members 350 may be provided by any of the techniques previously described herein, such as by deployment of a sheath means, a permanent sheath which is permeable or semi-permeable to fluids, or by modifying the design of the end members or central member to provide fluid access to the expandable members.

Figure 23B:
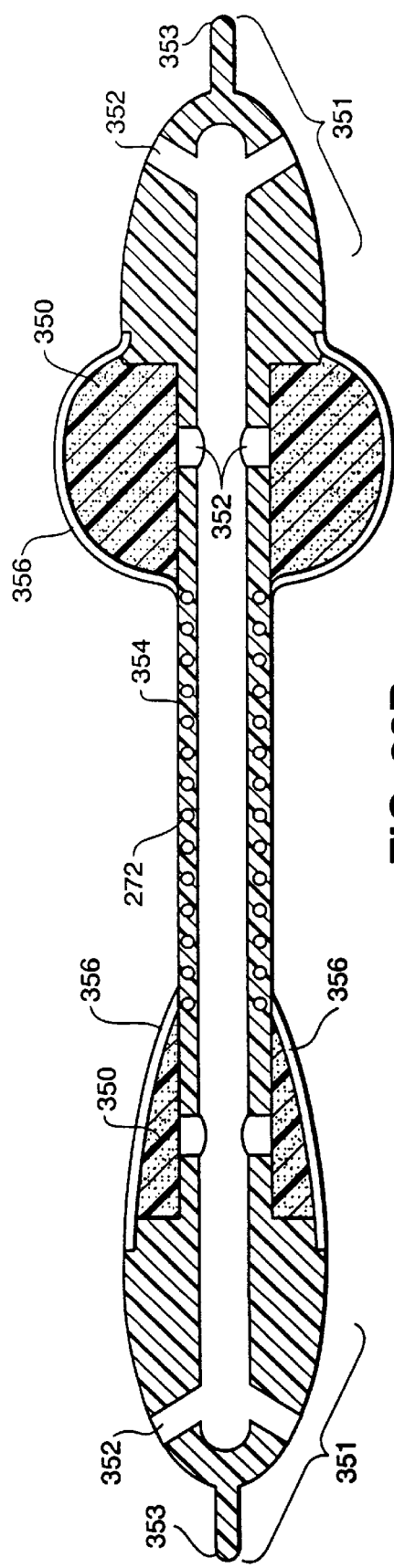
Figure 23C:
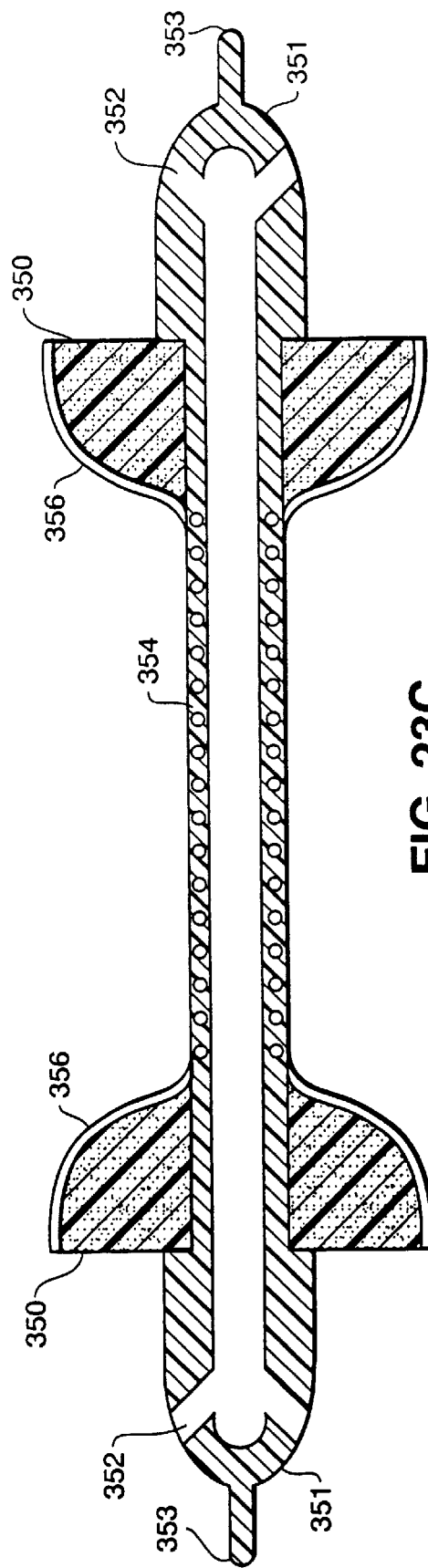

Referring to FIG. 23B, in another embodiment the sheath means 356 is permanently affixed to the exterior of the expandable members 350. Expansion of the members 350 is likewise achieved by exposure to fluids, however, the fluid source comes from within the central member 354 by openings 352 located beneath the expandable members 350. Fluid passing through openings 352 encounters the underside of the expandable members 350 causing them to expand such that the sheath means 356 abuts the interior of the vessel. Referring to FIG. 23C, a similar resulting configuration can be provided without the necessity for openings 352 to be in fluid communication with the expandable members by providing a semi-permeable sheath means, preferably formed of a flexible thin polymer sheet that may have a dissolvable coating, such that fluid causes the expandable members to expand by slowly penetrating the sheath means from the exterior thereof.

Figure 24A:
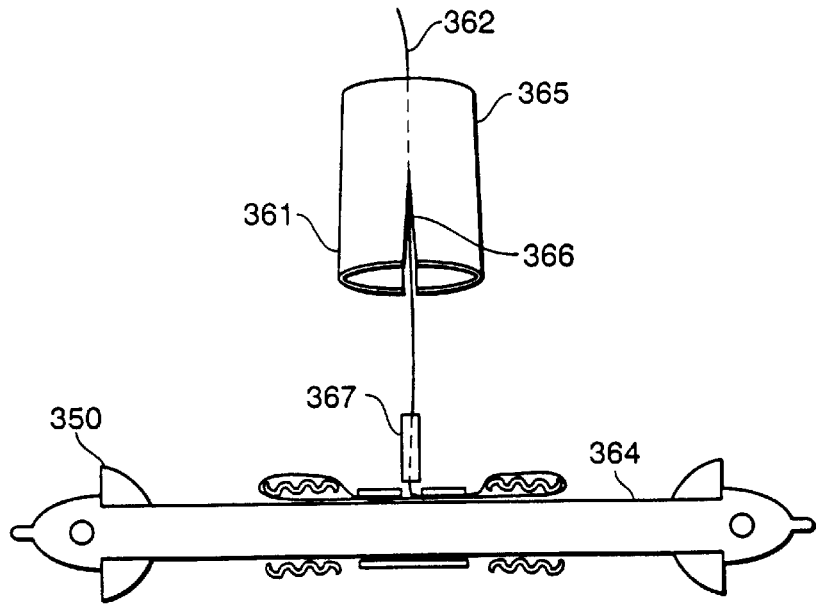
FIGS. 24A through 24C shows the device having means for retrieving the shunt comprised of a shunt remover operably associated with the suture.
Figure 24B:
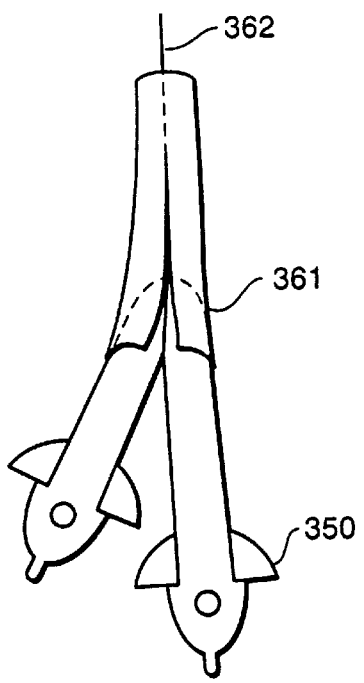
Figure 24C:
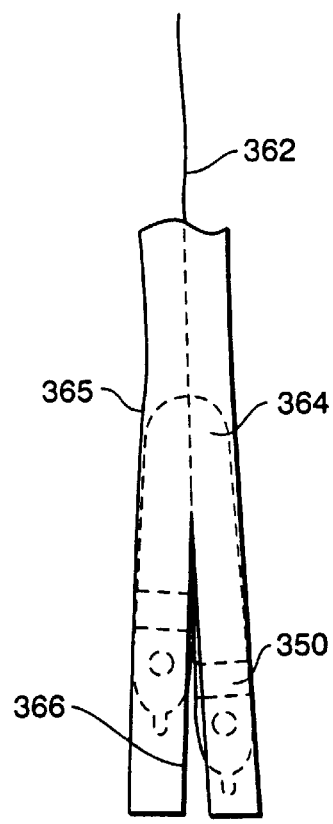

Referring to FIGS. 24A, 24B, and 24C, removal of a shunt having a flexible central member 364 from within the arteriotomy may be facilitated by a removal device 365 which is preferably integral with a thread 362 attached to the shunt of the invention. The shunt remover 365 may be comprised of a substantially cylindrical hollow body 360 having a stretchable tapered end portion 361 for easy insertion between sutures. Tapered end portion 361 is also made of a flexible or stretchable material, such as polyurethane, polyester, PEBA, polyethylene, etc. to ease drawing the shunt into the body of the shunt remover. The shunt may be drawn into the body of the shunt remover 365 by applying tension to thread 362 which is attached to the shunt, and is preferably larger in diameter, i.e., double the outer diameter of the central member 364. Thread 362 is also attached to the shunt at a point off-center (not shown) so that expandable members 350 exit the arteriotomy one at a time, or sequentially, to avoid stretching the arteriotomy and to avoid jamming within shunt remover 365. At the completion of the use of the shunt, the shunt remover would be advanced to the arteriotomy site and placed against the central member 264 at the point where the thread is attached to the central member. As shown in FIG. 24B, by contacting the central member 364 of the shunt with the body of the shunt remover 365 and exerting tension on the thread 362, the central member 364 collapses and is drawn into the body of the shunt remover 365 as shown in FIG. 24C. By this design and technique, the shunt is readily removed from the vessel through the arteriotomy, in a single step, without the necessity to manipulate the shunt, thereby reducing the possibility of damaging the vessel.

The body 360 of the shunt remover 365 may have an opening, preferably formed as a slit 366, running the length of the cylindrical portion of the body 360 of the remover 365 to ease the insertion and manipulation of the shunt remover 365 about the thread 362. Alternatively, the slit 366 may extend through only a portion of the cylindrical body 360 of the shunt remover 365. If desired, a similar device (not shown) can be used as a shunt insertion tool by providing a plunger within the body 360 and by folding an unused shunt and positioning it in the body thereof. By depressing the plunger the shunt is directed into the vessel. A stop may also be positioned at the distal end and placed inside the vessel to direct insertion of the shunt into the vessel by deflecting the tips in either direction.

In embodiments where a removable sheath means are used, the sheath remover 365 may have associated therewith a sheath remover 367 preferably traversed by the thread 362 and located intermediate of the shunt and shunt remover 365. The diameter of the shunt remover is smaller than the diameter of the central member 364. Using the sheath remover 367, the sheath means are removed by bringing the sheath remover 367 into contact with the central member 364 at the point of attachment to the thread 362. Because the inner-diameter of the sheath remover 367 is smaller than the central member 364 of the shunt, by exerting tension on the thread 362, the sheath means are removed from about the expandable members 350.

Figure 25:
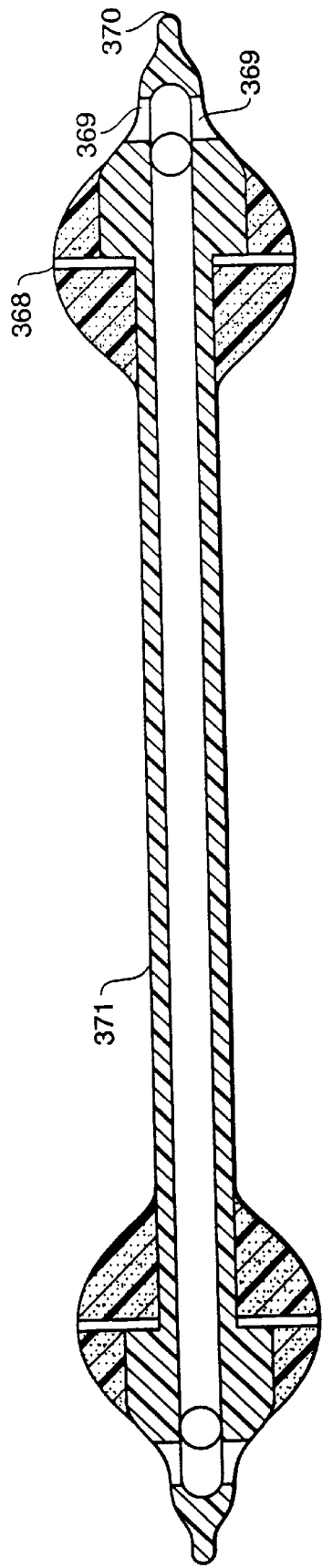
FIG. 25 is a preferred embodiment of the invention having rounded end members and which is designed to be manufactured in discrete sizes for selection by the surgeon depending on the interior dimension of the target vessel of the anastomosis.

Referring to FIG. 25, a preferred embodiment of the invention is shown which is similar to the embodiment of FIG. 3 and has rounded end members 368 to engage the interior surfaces of the vessel, perfusion holes 369 distal to the rounded portion of the end members 368, and a tip distal to the perfusion holes 369 to facilitate placement of the device in the vessel. This configuration is preferred for ease of manufacture and is specifically contemplated to be manufactured in discrete and varying sizes depending on a clinical assessment of the physiology of an individual patient. Typically, the outer diameter of the device at its maximum point, the point of the maximum diameter of the rounded end members, varies from approximately 1.5 mm to 5.0 mm. In use, the selection of the proper size of the device of the invention may be achieved by visual inspection or by mechanical measurement of the vessel interior at the site of the arteriotomy. The device is preferably provided with a thread line affixed to the central member to facilitate removal of the device.

In addition to providing a separate fixture to remove the shunt, a similar, related device can be used to insert the shunt into the vessel through the arteriotomy and to position the shunt in preparation for the anastomosis. As with the body of the shunt remover, the shunt insertion tool has a body which is preferably greater than twice the largest outer diameter of the central member of the shunt. The shunt is placed in the body at the distal end where an opening exists. Within the body of the shunt insertion tool, a slidable member engages the shunt and pushes the shunt out of the body of the insertion tool and into the vessel. Preferably, the shunt is doubled over within the body of the insertion tool such that approximately the mid-point of the shunt is most proximal to the surgeon and the ends of the shunt are most distal and may extend slightly from the opening at the distal end of the shunt insertion tool. To deploy the shunt, the slidable member is moved downward to abut the shunt within the body of the insertion tool such that approximately the mid-point of the shunt is most proximal to the surgeon and the ends of the shunt are most distal and may extend slightly from the opening at the distal end of the shunt insertion tool. To display the shunt, the slidable member is moved downward to about the shunt within the body of the insertion tool to force the shunt out of the insertion tool and into the vessel. While the distal end of the insertion tool may be comprised of a simple opening, the distal end may also have guides to facilitate atraumatic insertion of the shunt into the vessel.

Although the invention has been described herein relative to specific embodiments and modifications, various additional features and combinations of those specifically described will be apparent from the description and drawings. Thus the scope of the invention is defined by the following claims and their equivalents.

What is claimed is:

1. A distal perfusion device for maintaining flow in a vessel having an incision in said vessel comprising:

a central member containing a lumen wherein substantially the entire length of said central member is formed of first and second sheets of radially expandable material of shape-memory property laminated together, wherein the memory of the first sheet establishes a curled cross section, said central member having end members affixed thereto and perfusion openings in communication with said lumen to maintain the blood flow through said vessel, and heating means integrally secured to said first and second sheets respectively to selectively heat the sheets in response to an electrical current to contract and expand the diameter of the central member.

2. A distal perfusion device for maintaining flow in a vessel having an incision in said vessel comprising:

a central member containing a lumen wherein said central member is formed of a radially expandable material comprising substantially the entire length of the central member and a radially flexible material at a portion of the central member, said central member having end members affixed thereto and perfusion openings in communication with said lumen to maintain the blood flow through said vessel;

a choker tube formed with the radially expandable material; and a thread extending through the choker tube to attach to said portion of the central member, whereby the tension on the thread draws the expandable material inward to decrease the diameter of the central member.

3. A distal perfusion device for maintaining flow in a vessel having an incision in said vessel comprising:

a central member containing a lumen wherein said central member is comprised of at least one wound coil and an elastomer material disposed about the coil and extending therebetween to define the structural support means of the central member, said central member having end members affixed thereto and perfusion openings in communication with said lumen to maintain the blood flow through said vessel.

4. The device of claim 3 wherein one end of the coil extends from an anastomosis site to allow application of a pulling force to said end to unravel the coil.

5. A distal perfusion device for maintaining flow in a vessel having an incision in said vessel comprising:

a central member containing a lumen, said central member having end members affixed thereto and perfusion openings in communication with said lumen to maintain blood flow through said vessel;

wherein said central member includes a flexible, loosely wound coil of a diameter generally corresponding to the diameter of said vessel, and means for providing an enlarged diameter of said device upon insertion of the device within said vessel, said means for providing an enlarged diameter including a coating of a flexible, fluid impervious material deposited about the coil to define a central lumen therethrough, said selectively tapered end members being comprised of coiled end portions having said coating of the flexible, fluid impervious material deposited thereon.

6. A distal perfusion device for maintaining flow in a vessel having an incision in said vessel comprising:

a central member containing a lumen, said central member having end members affixed thereto and perfusion openings in communication with said lumen to maintain blood flow through said vessel, wherein said central member is formed in two separate portions each with respective tapered end members, and wherein said separate portions are insertable individually into said vessel through the arteriotomy and subsequently joined together within said vessel.

7. A distal perfusion device for maintaining flow in a vessel having an incision in said vessel comprising:

a central member containing a lumen, said central member having end members affixed thereto and perfusion openings in communication with said lumen to maintain blood flow through said vessel, wherein each of said end members has a tip distal to said perfusion openings and wherein a selectively tapered end member has a guide opening in a conical wall thereof, and a guide wire threaded through the guide opening and the end member and through the incision into said vessel;

wherein said guide wire facilitates the insertion of the device distally into said vessel.

8. A distal perfusion device for maintaining flow in a vessel having an incision in said vessel comprising:

a central member containing a lumen, said central member having end members affixed thereto and perfusion openings in communication wit said lumen to maintain blood flow through said vessel, and wherein said central member is formed with an arcuate portion removed therefrom diametrically opposite the anastomosis site to define a necked-down section of said central member.

9. A distal perfusion device for maintaining flow in a vessel having an incision in said vessel comprising:

a central member having a diameter and containing a lumen wherein said central member is formed of a pair of coaxially spaced flexible coils said central member having end members affixed thereto and perfusion openings in communication with said lumen to maintain blood flow through said vessel;

a coating of elastomer material laminated about said coils and extending therebetween to form said central member;

a choker tube secured to the central member and extending therefrom; and thread means secured to facing ends of the coils and extending through the choker tube, wherein force applied to the thread means axially stretches the coils to contract the shunt diameter and releasing the thread means allow the shunt diameter to expand.

* * * * *